(12) United States Patent
Furenlid et al.

(10) Patent No.: US 11,819,346 B2
(45) Date of Patent: *Nov. 21, 2023

(54) SCINTILLATION DETECTOR BASED SYSTEMS AND METHODS FOR USING THE SAME

(71) Applicants: Lars Furenlid, Tucson, AZ (US); Xin Li, Tucson, AZ (US)

(72) Inventors: Lars Furenlid, Tucson, AZ (US); Xin Li, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 73 days.

This patent is subject to a terminal disclaimer.

(21) Appl. No.: 17/700,442

(22) Filed: Mar. 21, 2022

(65) Prior Publication Data

US 2022/0211334 A1 Jul. 7, 2022

Related U.S. Application Data

(63) Continuation-in-part of application No. 16/345,682, filed as application No. PCT/US2017/058501 on Oct. 26, 2017, now Pat. No. 11,385,362.

(60) Provisional application No. 62/414,469, filed on Oct. 28, 2016.

(51) Int. Cl.
*A61B 6/03* (2006.01)
*G01T 1/202* (2006.01)
*A61B 6/00* (2006.01)
*G01T 1/20* (2006.01)

(52) U.S. Cl.
CPC ............ *A61B 6/037* (2013.01); *A61B 6/4258* (2013.01); *G01T 1/202* (2013.01); *G01T 1/20181* (2020.05); *G01T 1/20185* (2020.05)

(58) Field of Classification Search
None
See application file for complete search history.

(56) References Cited

U.S. PATENT DOCUMENTS 10,042,058 B2 * 8/2018 Moskal ................. G01T 1/1642
11,385,362 B2 * 7/2022 Furenlid ............ G01T 1/20182

* cited by examiner

*Primary Examiner* — Edwin C Gunberg
(74) *Attorney, Agent, or Firm* — Quarles & Brady LLP; Yakov S. Sidorin

(57) ABSTRACT

A scintillation-crystal based gamma-ray detector with photon sensors disposed on edge surface(s) of the crystal to take advantage of total internal reflection of scintillation photons within the thin-slab detector substrate to improve spatial resolution of determination of a scintillation event (including depth-of-interaction resolution) while preserving energy resolution and detection efficiency. The proposed structure benefits from the reduced—as compared with related art—total number of readout channels elimination of need in complicated and repetitive cutting and polishing operations to form pixelated crystal arrays used in conventional PET detector modules. Detectors systems utilizing stacks of such detectors, and methods of operation of same.

17 Claims, 29 Drawing Sheets

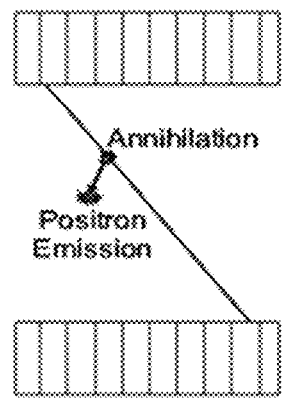
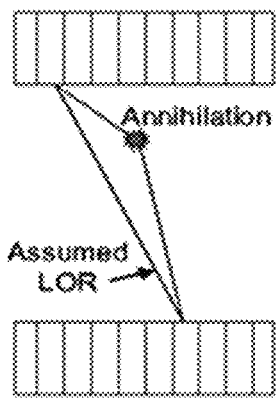
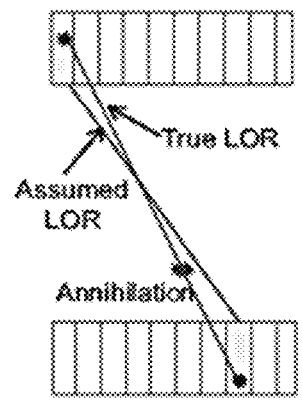
FIG. 4A            FIG. 4B            FIG. 4C
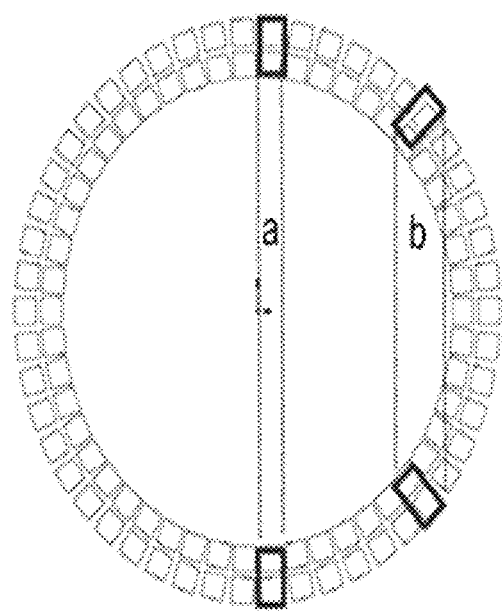
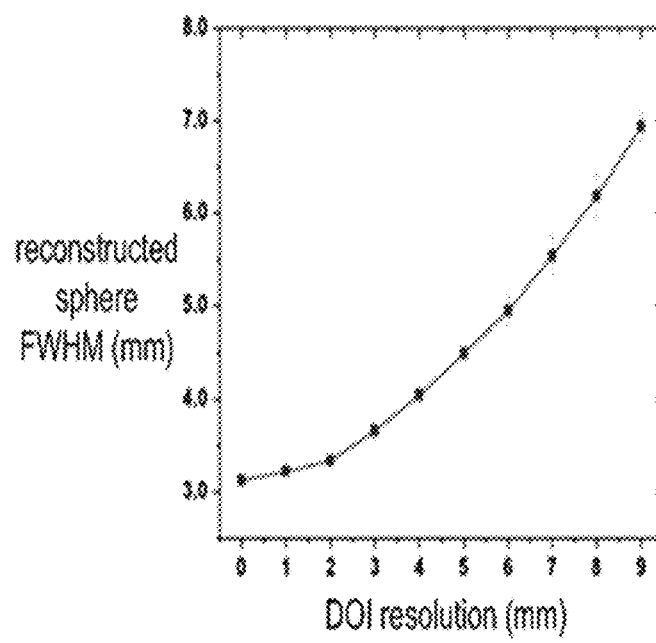
FIG. 5              FIG. 6

Pixelated camera

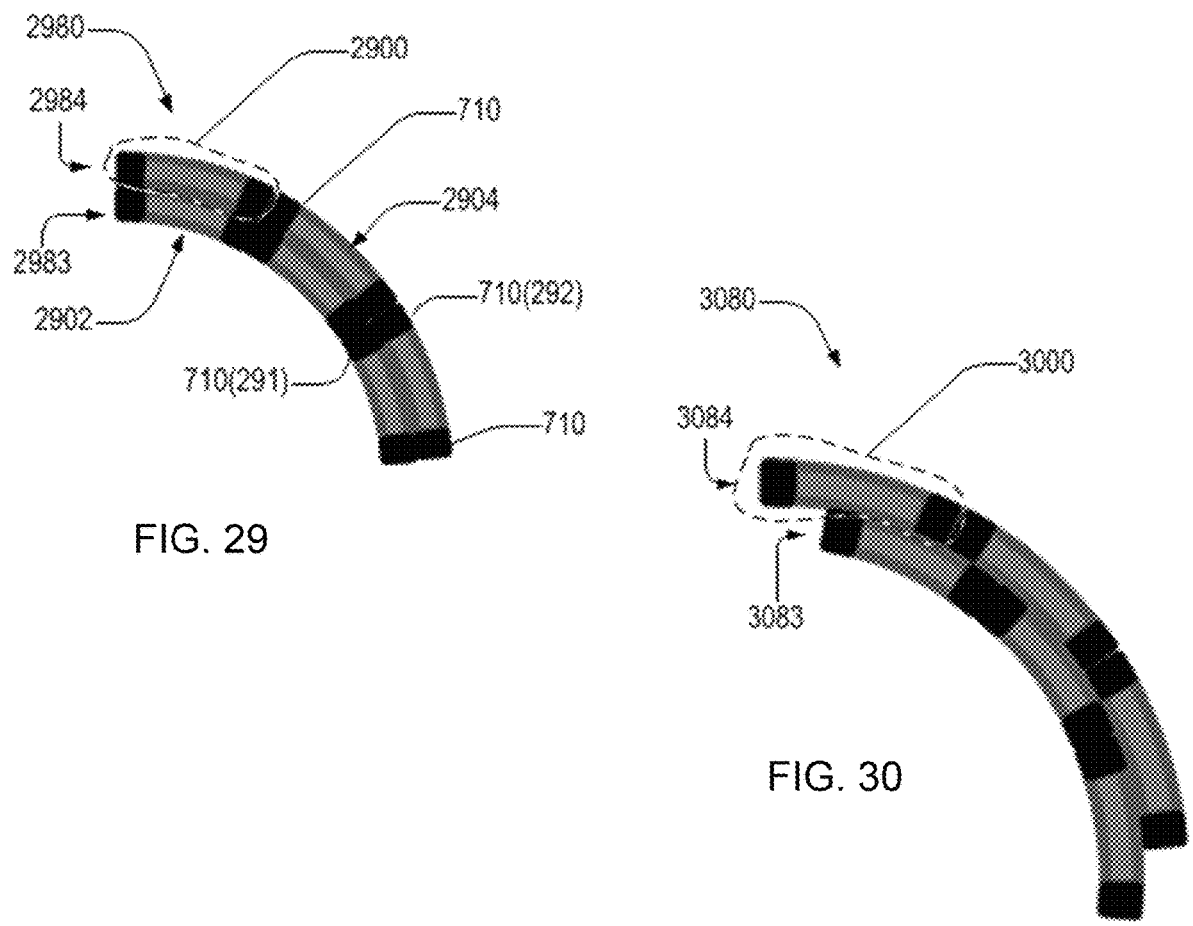
FIG. 29
FIG. 30
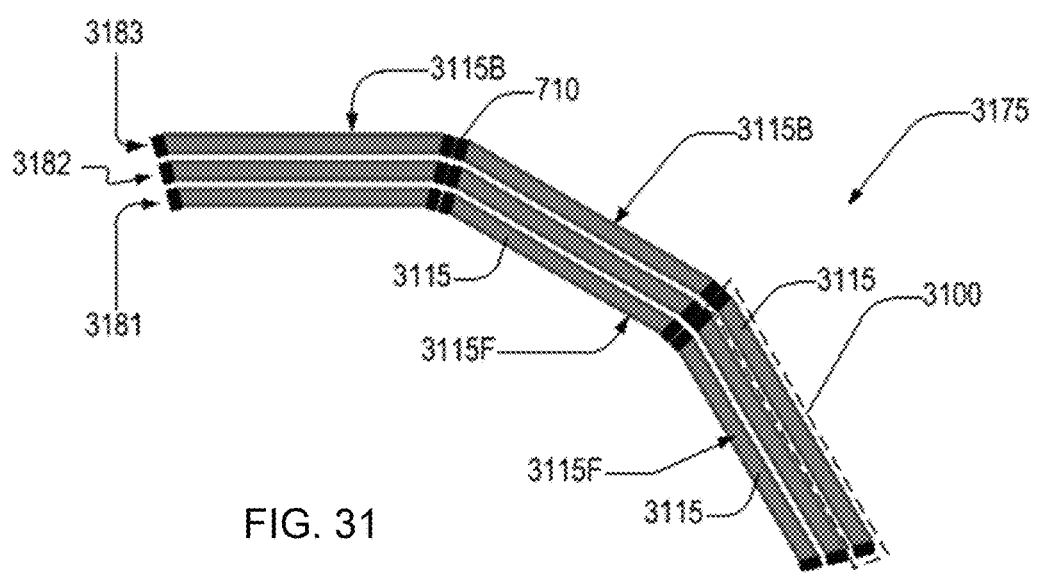
FIG. 31

SCINTILLATION DETECTOR BASED SYSTEMS AND METHODS FOR USING THE SAME

CROSS-REFERENCE TO RELATED APPLICATIONS

The present US patent application is a continuation-in-part from the U.S. patent application Ser. No. 16/345,682 filed on Apr. 26, 2019 and now published as US 2019/0353807, which is a national phase from the International Patent Application No. PCT/US17/58501 filed on Oct. 26, 2017 and now published as WO 2018/081404, which in turn claims priority from the U.S. Provisional Patent Application No. 62/414,469 filed on Oct. 28, 2016. The disclosure of each of the above-identified patent documents is incorporated herein by reference.

STATEMENT REGARDING FEDERALLY SPONSORED RESEARCH OR DEVELOPMENT

This invention was made with government support under Grant No. P41 EB002035, awarded by NIH. The government has certain rights in the invention.

BACKGROUND OF THE INVENTION

Positron Emission Tomography (PET) has become a mature and reliable technology. It has broad applications in neurology and oncology due to its ability to monitor metabolism of glucose and the uptake of other targeting radiotracers in specific organs and tissues. Compared with alternative technologies (functional MRI, CT, and SPECT), the sensitivity of PET is several orders of magnitude higher, which ensures more reliable measurement results (in terms of, for example, lower noise, better spatial resolution, better contrast to noise ratio, etc.).

FIG. 1 illustrates a conventional PET detector 100. It includes a pixelated scintillator block and associated photon detection sensors (e.g., photomultiplier tubes or silicon photomultipliers). If a gamma-ray photon is absorbed inside one of the pixels, visible scintillation photons are produced and propagate to photon sensors guided by reflections at crystal surfaces. By the proportion of light detected by the photon sensors, the gamma-ray photon's energy, interaction pixel and interaction time may be estimated.

FIG. 2 depicts a detector ring 200 formed from hundreds of PET detectors 100. In medical practice, detector ring 200 surrounds a patient. FIG. 3A illustrates an idealized version of a PET, where a radioactive atom emits a positron 301 that, before traveling any distance, encounters an electron resulting in an annihilation event occurring at an annihilation position 303. The annihilation results in emission of two gamma-ray photons 305(1, 2) collinearly travelling in opposite directions from annihilation position 303.

FIG. 3B depicts a non-ideal PET scenario that radiologists encounter, where a positron is emitted by a radioactive atom, and after the positron travels a short distance 307 (positron range is mentioned in limitation 1 below), it combines with an electron, which combination results in annihilation. The electron and positron combine and convert to two gamma-ray photons 309(1, 2) emitted from the annihilation position. However, the two gamma-ray photons do not travel in exactly opposite directions. Rather, there is generally a very small angular deviation from 180°, between the directions of propagation of two gamma-ray photons. This is referred to as a non-collinearity effect as mentioned in limitation 1.

If both gamma-ray photons are detected, the position of the annihilation event is typically somewhere along the line connecting the two gamma-ray photons' interaction positions on the detector ring. This line is referred in related art to as the line of response (LOR). By identifying a sufficient number of lines of response, an image of the isotope map marking a certain organ or tumor may be reconstructed with known algorithms (such as filtered back projection (FBP) or maximum likelihood estimation (MLE) algorithms, for example).

FIG. 4 (panels a, b and c) illustrates influence of positron range, non-collinearity, and depth of interaction (DOI) on accurate estimation of the LOR. According to FIG. 4, panel c, when DOI information is not available, the LOR is typically assigned to the fixed positions of the scintillation crystals. However, this may result in a somewhat incorrectly assigned LOR due to parallax error. If accurate DOI information is available, the true LOR may be determined.

As compared with traditional SPECT technology, the PET has much greater sensitivity since the implementation of it does not require the use of collimators. Compared with functional MRI or CT, the sensitivity of the PET methodology is usually several orders of magnitude higher. However, PET technology still has some limitations. These limitations include:

Limitation 1: The positron range and non-collinearity degrades the spatial resolution. Since the annihilation position is different from the radioactive isotope's position because the positron travels a small distance before it combines with an electron (positron range effect), there is error or blur in the reconstructed image. Also, due to the non-collinearity effect, the annihilation position further deviates from the ideal line of response.

Limitation 2: Making the pixelated crystal's cross section small can be very challenging. Due to the high energy of gamma-ray photons, they are very difficult to stop. A thicker crystal should be utilized to efficiently stop the majority of the gamma-ray photons. However, this makes the pixelated crystal's aspect ratio low. The smaller the pixel's pitch size, the larger the number of reflections required for a photon to travel to the photon sensors, which will decrease the light output amount due to the losses from reflections.

Limitation 3: The depth of interaction estimation is critical for accurate measurement. The depth of interaction is important, since it affects the spatial resolution at the edge of the field of view. As shown in FIG. 5, if the two detector elements on opposite sides of the detector ring detect two corresponding gamma-ray photons simultaneously, the annihilation position is within region a indicated in FIG. 5. However, if the two detector elements on the right simultaneously detects two gamma-ray photons, the annihilation position is within region b. Compared with the annihilation in region a, the one in region b creates more ambiguity due to the lack of depth of interaction information. Moreover, as can be seen in the plot of FIG. 6, reconstructed spatial resolution worsens (size of smallest resolvable feature increases) as the DOI resolution gets worse, and this effect is obvious as the spatial resolution decreases with the distance from the center of field of view increases.

Limitation 4: The current cost of manufacturing pixelated crystals is extremely high. Since pixelated crystals need special surface treatment (insulating, polishing) between individual pixels, the cost of manufacturing such crystals is high. Moreover, if the pixels are smaller than about 1 mm, the difficulty in special treatments drives the cost even higher.

Limitation 5: The sensitivity is reduced due to the dead-area gap caused by crystal pixelating. Due to the pixels, a gap is needed to properly insulate the scintillation photons from propagating into adjacent pixels. This gap will decrease the detection efficiency of the detector to gamma-ray photons. Especially for smaller pixel pitches, since the gap width almost remains constant, the fraction of the gap width/pixel pitch will be larger, and the detection efficiency is even lower.

SUMMARY OF THE INVENTION

Implementations of the present invention provide improved scintillation-crystal based gamma-ray detectors, scintillation systems that include stacks of such detectors, and PET detector rings and arrays that take advantage of collection of scintillation photons with the use of total internal reflection within the substrate of a constituent scintillation detector. The disclosed detector systems and arrangements and methods of employments of such arrangement provide improved spatial resolution—including depth-of-interaction (DOI) resolution—while preserving energy resolution and detection efficiency, which is especially useful in small-animal or human positron emission tomography (PET) or other techniques that depend on high-energy gamma-ray detection. Additionally, implementation of the present invention advantageously reduce the total number of required readout channels and reduce the need to do complicated and repetitive cutting and polishing operations to form pixelated crystal arrays as is the standard in current PET detector modules, as compared with related art.

Embodiments of the invention provide a scintillation detector that includes a scintillator element configured as a monolithic optical substrate of a scintillation crystal material. (Such substrate is dimensioned as a thin slab and is materially limited by a front surface configured as an input surface of the detector, a back surface separated from the front surface by a thickness of the monolithic substrate, and an edge surface connecting the front and back surfaces.) The scintillation detector also includes multiple photodetectors, each of which is disposed to acquire the scintillation photons from the body of the element through a respectively-corresponding section of the edge surface. The monolithic substrate in configured as a lightguide channeling the scintillation photons generated in the substrate by radiation, which has entered the substrate through the input surface, along the input surface towards and through the edge surface to be acquired by the multiple photodetectors. In one embodiment, the scintillation detector includes a microprocessor, operably cooperated with the multiple photodetectors, and a tangible non-transitory storage medium on which are stored data-processor-readable instructions such that (when the instructions are executed by the microprocessor of a data processor) the instructions cause the microprocessor to estimate lateral coordinates, in a plane of the monolithic substrate, of a location of a scintillation event based on a plurality of amplitudes of electrical signals received from the multiple detectors and respective plurality of locations of the multiple photodetectors, to estimate energy of the scintillation event, and to estimate time of occurrence of the scintillation event.

Embodiments of the invention also include a positron emission tomography (PET) detector ring that contains a first ring-shaped array of first scintillation detector assemblies (here, each first scintillation detector assembly includes an embodiment of the scintillation detector, or a scintillation detector system that contains a stack of such scintillation detectors that are separated, from an immediately-neighboring scintillation detector in the stack, by a gap in a direction transverse to respectively-corresponding front surfaces of monolithic substrates of the scintillation detectors).

Suitable photodetectors include, but are not limited to, silicon photomultipliers (SiPMs), photomultiplier tubes (PMTs), and complementary metal-oxide semiconductor (CMOS) sensors. The photodetectors may further comprise an avalanche photodiode (APD). In an embodiment, the photodetectors comprise SiPMs, APDs, or combinations thereof. In an embodiment, the photodetectors comprise SiPMs.

An embodiment of the present invention provides a plurality of scintillation detectors arranged as a stack, the plurality of scintillation detectors comprising a first scintillation detector and a second scintillation detector, the back substrate-surface of the first scintillation detector being adjacent to, opposing, and optionally spatially separated from the front substrate-surface of the second scintillation detector. In further embodiments, the stack comprises two or more, three or more, four or more, five or more, six or more, seven or more, eight or more, nine or more, ten or more, fifteen or more, or twenty or more scintillation detectors. In a further embodiment, optically opaque materials or optically reflecting materials are positioned between portions of two or more of the scintillation detectors to reduce transmission of light between different scintillation detectors, thereby limiting optical cross-talk between the different detectors. Suitable optically opaque materials include but are not limited to thin metal layers (such as aluminum foil), ceramics, plastic, cloth, and paper. Optically opaque materials may be painted, dyed, or otherwise colored to be black or another color so as to reduce or eliminate transmission of light.

The stacking or tiling of layers of scintillation detectors may be offset by a small distance to compensate for the gaps between detector layers. For example, the second scintillation detector may be positioned in relation to the first scintillation detector such that a center region of the second scintillation detector is aligned with a center region of the first scintillation detector relative to an axis perpendicular to the front substrate-surface of the first scintillation detector. Alternatively, the second scintillation detector may be positioned in relation to the first scintillation detector such that a center region of the second scintillation detector is laterally offset from center region of the first scintillation detector relative to an axis perpendicular to the front substrate-surface of the first scintillation detector. Alternatively, the second scintillation detector is positioned in relation to the first scintillation detector such that a center region of the second scintillation detector is aligned with an edge surface of the first scintillation detector relative to an axis perpendicular to the front substrate-surface of the first scintillation detector.

In a related embodiment, multiple stacks of scintillation detectors may be arranged adjacent to one another. The scintillation detectors within a given stack may have different lateral lengths to allow multiple stacks to be arranged adjacent to one another in a non-linear geometry.

An embodiment of the present invention provides a positron emission tomography (PET) detector ring having a plurality of scintillation detectors comprising a scintillator substrate and a plurality of photodetectors. The scintillator substrate for each scintillation detector has an interior bound by a front surface having a front perimeter, a back surface opposite the front surface and having a back perimeter, and an edge surface between the front and back perimeters. Each of the plurality of photodetectors is disposed on one of a respective plurality of regions of the edge surface, and each having a field of view that includes a portion of the interior. In an embodiment, the PET detector ring comprises two or more, three or more, four or more, five or more, six or more, seven or more, eight or more, nine or more, ten or more, fifteen or more, twenty or more, fifty or more, or a hundred or more scintillation detectors. At least a first sub-plurality of the plurality of scintillation detectors form a first array having (i) a first concave inward-facing surface and including each front surface of the first sub-plurality and (ii) a first convex outward-facing surface and including each back surface of the first sub-plurality. The second array may be spatially shifted from the first array such that photons transmitted between photodetectors of adjacent scintillation detectors of the first array are incident on a substrate of a scintillation detector of the second array.

In a further embodiment, the plurality of scintillation detectors comprise a second sub-plurality of scintillation detectors forming a second array having (i) a second concave inward-facing surface, opposite the first convex outward-facing surface, and include each front surface of the second sub-plurality of scintillation detectors and (ii) a second convex outward-facing surface that includes each back surface of the second sub-plurality of scintillation detectors.

In further embodiments, the substrates of the scintillation detectors, stacks, and detector rings comprise a plurality of optical scatterers (which may be also interchangeably referred to herein as optical barriers). Optical scatterers may be any inclusion, treatment, or modification to the inside of the substrate or on the surface of the substrate, where the inclusion, treatment, or modification is able to absorb or redirect light to reshape the mean detector response function (MDRF). For example, the optical scatterers may comprise, but are not limited to, a through hole, a blind hole, an object on the front surface, an object on the back surface, a volume with modified optical properties generated by laser etching or laser engraving, or combinations thereof. The optical scatterers may have any shape or pattern, as long as they are able to reshape the MDRF. In certain embodiments, each of the plurality of optical scatterers may have an extent exceeding a wavelength corresponding to an emission maximum of the scintillator material. In certain embodiments, the optical scatterers may utilize Rayleigh scattering, where the size of particles forming the optical scatterers is smaller than the dimension of the wavelength of light. In certain embodiments, the dimension or size of the optical scatterers may be close to the wavelength of the scintillation emission maximum, in which case certain interference patterns may form on the edges of the detector, which helps determine the positioning of the gamma-ray photons. For example, a plurality of small optical scatterers with size or inter-scatterer spacing close to the emission wavelength can create interference similar to that formed by an optical lens. This "virtual" lens can be used to reshape the MDRF of the detector, which helps to increase the capability for determining the position of the gamma-ray photons.

The scintillation detectors, stacks, and detector rings described herein may further comprise a memory storing non-transitory computer-readable instructions; and a microprocessor adapted to execute the instructions to estimate lateral coordinates, in a plane of the substrate, of a scintillation-event interaction-position based on a plurality of electrical signal amplitudes and respective plurality of locations of the plurality of photodetectors. Optionally, the microprocessor is configured to receive electrical signals generated by one or more scintillation events from the plurality of photodetectors, and is configured to estimate lateral coordinates of a scintillation-event interaction-position in a plane of the substrate of the at least one of the plurality of scintillation detectors, based on a plurality of electrical signal amplitudes and respective plurality of locations of the plurality of photodetectors. Optionally, the microprocessor is further configured to estimate depth coordinates of a scintillation-event interaction-position based on the plurality of electrical signals and respective plurality of locations of the plurality of photodetectors within the stack.

An embodiment of the present invention provides methodologies for determining the interaction position of a scintillation event occurring in a substrate resulting from electromagnetic radiation incident on a front surface of the substrate, as discussed in US 2019/0353807 (the disclosure if which is incorporated herein by reference).

BRIEF DESCRIPTION OF THE DRAWINGS

FIG. 4 (panels a, b and c) illustrates, respectively, the effect produced by including a positron range, non-collinearity, and a depth of interaction information (DOI) on accuracy of estimation of the annihilation position on the correct line of response.

FIG. 5 illustrates two possible positron-electron annihilation regions within the detector ring of FIG. 2, which result in different measurement ambiguity due to the lack of depth of interaction (DOI) information.

FIG. 6 is a plot showing spatial resolution of a reconstructed image as a function of depth-of-interaction (DOI) resolution.

FIG. 29 and FIG. 30 are cross-sectional views of embodiments of stacked scintillation detectors (aligned and offset, respectively), where individual/constituent scintillation detectors are curved.

FIG. 31 is a cross-sectional view of an embodiment of stacked scintillation detectors, where multiple tapered scintillation detectors are arranged laterally adjacently to each other in a configuration other than a flat planar configuration.

DETAILED DESCRIPTION OF THE INVENTION

Modern hard X-ray and gamma-ray detectors generally employ either scintillation-based or semiconductor-based components. During the last two decades, much progress has been made in the field of room-temperature semiconductor detectors such as CdZnTe, but these still face major challenges as compared with scintillation detectors. The challenges include high cost to manufacture large-area detectors (Takahashi, Tadayuki, and Shin Watanabe. "Recent progress in CdTe and CdZnTe detectors." *Nuclear Science, IEEE Transactions on* 48.4 (2001): 950-959), relatively lower detection efficiency (Chen, H., et al. "CZT device with improved sensitivity for medical imaging and homeland security applications." *SPIE Optical Engineering+ Applications*. International Society for Optics and Photonics, 2009), relatively poor timing resolution (Meng, Ling J., and Zhong He. "Exploring the limiting timing resolution for large volume CZT detectors with waveform analysis." *Nuclear Instruments and Methods in Physics Research Section A: Accelerators, Spectrometers, Detectors and Associated Equipment* 550.1 (2005): 435-445) and complicated readout ASICs (Peng, Hao, and Craig S. Levin. "Recent developments in PET instrumentation." *Current Pharmaceutical Biotechnology* 11.6 (2010): 555). The scintillation-detection technique thus remains dominant in modern clinical and preclinical SPECT and PET systems. However, as described below, it is still possible to enhance the performance of scintillator detectors. Most scintillation detectors employ monolithic crystals or pixelated crystals to which photon sensors are attached to the front or back surfaces to collect light and use the scintillation information for calculation of the event's position, energy, and time of interaction. Recently, silicon photomultipliers (SiPMs) have been made more compact and to possess smaller dark count rate, less cross talk, higher photon detection efficiency, higher gain, and broader spectral response. These advances enable new scintillation detector geometries proposed and discussed below for the first time. For example, the thin sides of monolithic scintillation crystals may be utilized as the photon readout surfaces.

Figure 1:
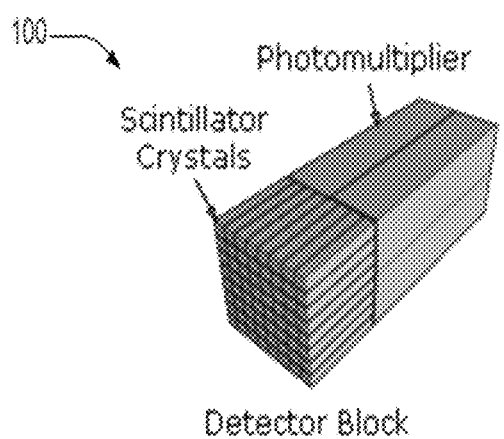
FIG. 1 illustrates a conventional positron emission tomography (PET) detector.
Figure 2:
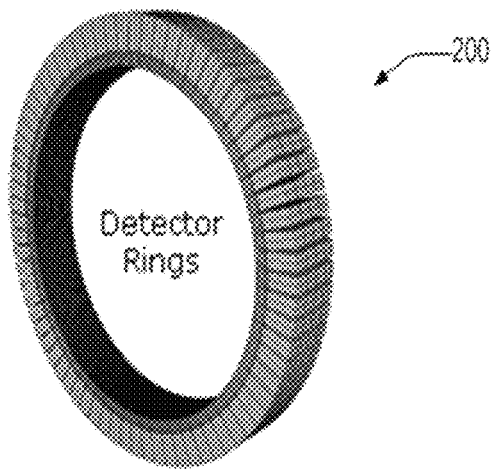
FIG. 2 by illustrates a detector ring formed from a plurality of the PET detectors of FIG. 1.
Figure 3A:
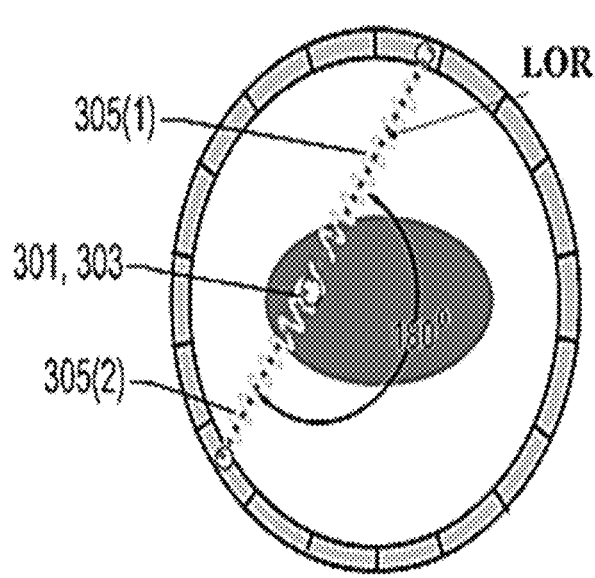
FIG. 3A and FIG. 3B illustrate a PET line of response with a zero positron range without non-collinearity effect and a non-zero positron range with non-collinearity effect, respectively.
Figure 3B:
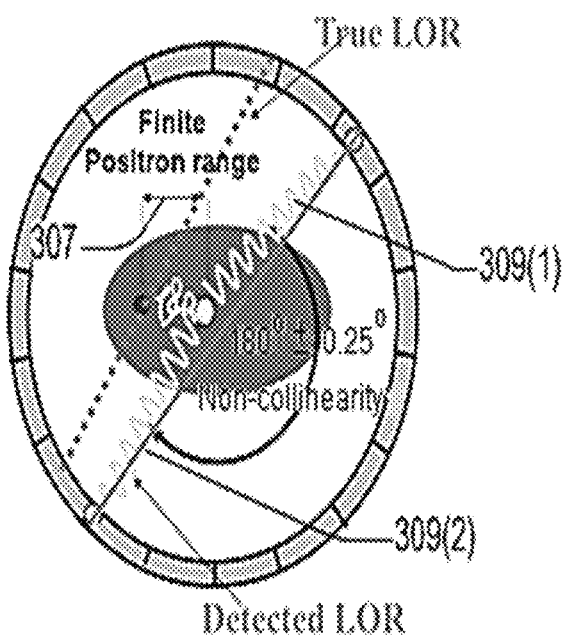
Figure 7:
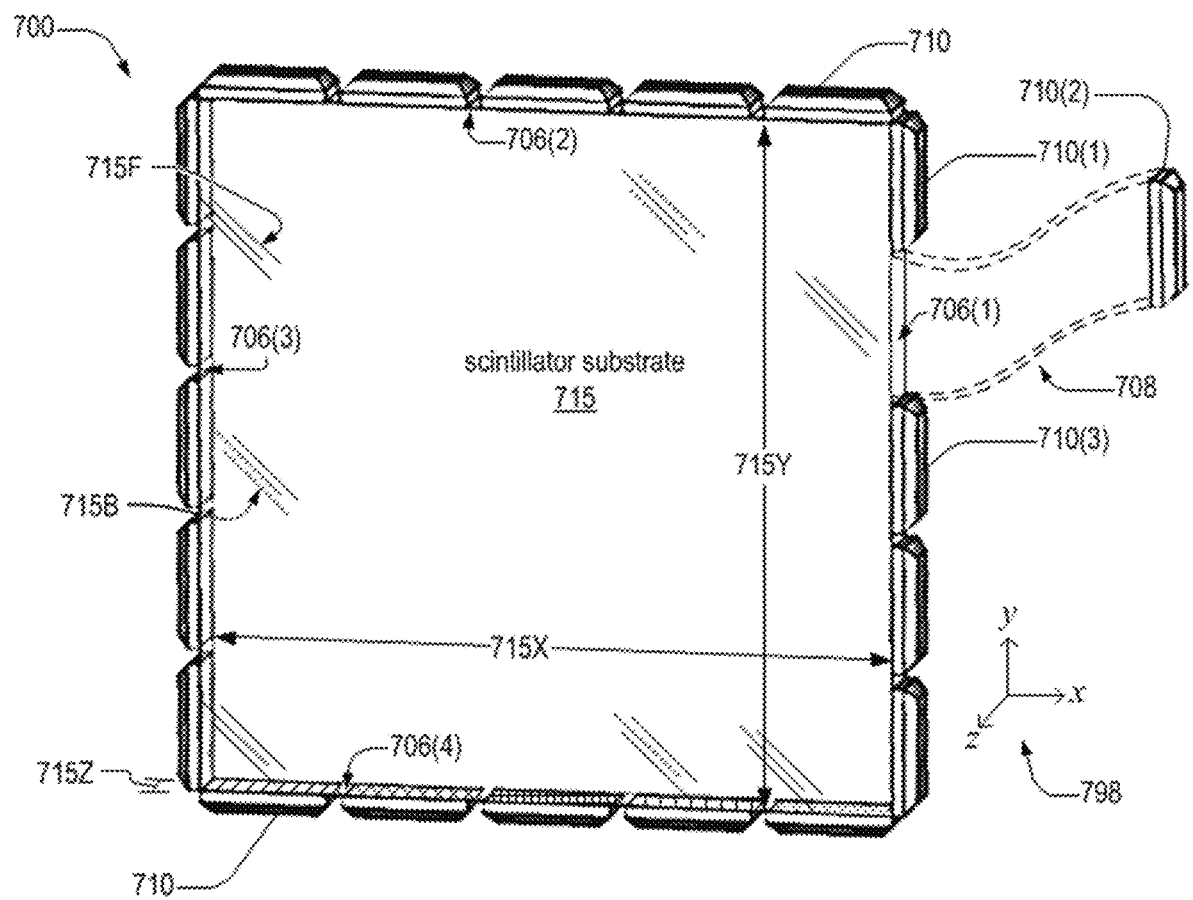
FIG. 7 illustrates an embodiment of a scintillation detector according to the idea of the invention, which does not contain any optical scatterers.

For example, and according to one idea of the present invention, FIG. 7 illustrates an embodiment of a scintillation detector 700 that includes a scintillator substrate 715 and a plurality of photodetectors 710. The scintillator substrate 715 has an edge surface 706. Each photodetector 710 has a photosensitive region in optical communication with one of a respective regions of edge surface 706.

FIG. 7 includes callouts for photodetectors 710(1) and 710(3), where photodetector 710(2) between the detectors 710(1), 710(3) is spatially separated from scintillator substrate 715 at least for illustration of the edge surface 706(2). FIG. 7 illustrates a coordinate system 798 that defines directions x, y, and z. Unless expressly stated otherwise, references to directions or planes denoted by at least one of x, y, or z refer to those indicated by the coordinate system 798. Scintillation detector 700 may also include a readout circuit and data processing unit communicatively coupled to the plurality of photodetectors.

Edge surface(s) 706 of the monolithic substrate 715 are between and connect a front surface 715F and a back surface 715B of scintillator substrate 715. Surfaces 715B, 715F are shown in this example to be parallel to the x-y plane. Each of front surface 715F and back surface 715B may be configured as planar, concave, or convex surface. Monolithic scintillator substrate 715 has spatial dimensions 715X, 715Y, and 715Z along respective directions x, y, and z. Spatial dimensions 715X and 715Y are, for example, between twenty millimeters and one hundred millimeters. Spatial dimension 715Z is, for example, between two millimeters and ten millimeters. In an embodiment, spatial dimensions 715X, 715Y, and 715Z are 15 to 150 mm, 15 to 150 mm, and 0.5-20 mm, respectively. In an embodiment, spatial dimensions 715X, 715Y, and 715Z are 50.4 mm±Δ, 50.4 mm±Δ, and 3.0 mm±δ, respectively, where Δ=5 mm and δ=2 mm. In an embodiment, spatial dimensions 715X, 715Y, and 715Z are 27.4 mm±Δ, 27.4 mm±Δ, and 3.0 mm±δ, respectively.

Candidate materials for scintillator substrate 715 include, but are not limited to, lutetium-yttrium oxyorthosilicate (LYSO), lutetium oxyorthosilicate (LSO), cesium iodide (CsI), sodium iodide (NaI), lanthanum(III) bromide ($LaBr_3$), yttrium aluminum perovskite (YAP), yttrium aluminum garnet (YAG), bismuth germinate (BGO), calcium fluoride activated by europium, lutetium aluminum garnet, gadolinium silicate doped with cerium, cadmium tungstate, lead tungstate, double tungstate of sodium and bismuth, zinc selenide activated with tellurium (ZnSe(Te)), and combinations thereof.

Each photodetector 710 may be a photodetector known in the art, for example, a photon sensor. Types of photon sensors include, but are not limited to, photomultipliers, such as silicon photomultipliers and photomultiplier tubes. In at least one embodiment, scintillator substrate 715 is made monolithic. Photodetectors 710 may be attached to an edge surface 706 via an adhesive, such as, but not limited to, an optical gel or by room-temperature-vulcanization (RTV) silicone. In a related embodiment, the light sensor may include a dedicated layer of window material, such as silicone epoxy. In an embodiment, the refractive index of the adhesive, window material, or combination thereof, are preferably disposed between the photon sensor material and the scintillation crystal.

Edge surfaces 706 may have a thin-film coating thereon formed between photodetectors 710 and edge surfaces 706. The thin-film coating may have at least one of an angle-dependent transmittance and an angle-dependent reflectance, which may be judiciously engineered to reshape the MDRF of detector 700 and hence increase accuracy of localization of the scintillation event. Candidate materials for the thin film coating include, but are not limited to, metals, ceramic materials, cermats, alloys, and combinations thereof. In certain embodiments, the thin film coating has an effect on reflection, refraction properties (such as angular dependence), and polarization properties.

One or more edge surfaces 706 may also be shaped to possess a surface roughness. Surface roughness may reduce measurement inaccuracies, e.g. high bias and variance, resulting from total internal reflection at edges of scintillator substrate 715. Part or all of a surface 706 may have a patterned surface roughness, such as cross-hatching, hatching or stripes, as illustrated in regions of edge surface 706(4), which may be beneath a detector 710 and/or between adjacent detectors 710. The hatching or stripes may be oriented at an angle (e.g., 90°) with respect to at least one of surfaces 715F and 715B. In one embodiment, the surface roughness is made sufficiently large for each edge surface 706 to be substantially a Lambertian surface. In an embodiment, the surface roughness has an Ra value higher than the wavelength of the emission peak. (As known in the art, "Ra" refers to average roughness and is the arithmetic average of the absolute values of the profile height deviations from a mean line.)

At least one photodetector 710 may be attached to scintillator substrate 715 such that its photosensitive region faces edge surface 706. Photodetectors 710 may include a photodetector spatially separated from scintillator substrate 715 and in optical communication with a region of edge surface 706. For example, detector 710(2) may be in optical communication with edge surface 706(1) through an optical coupler 708. Optical coupler 708 may include a waveguide, such an optical fiber, prism, lens, mirror or combinations thereof.

Figure 8:
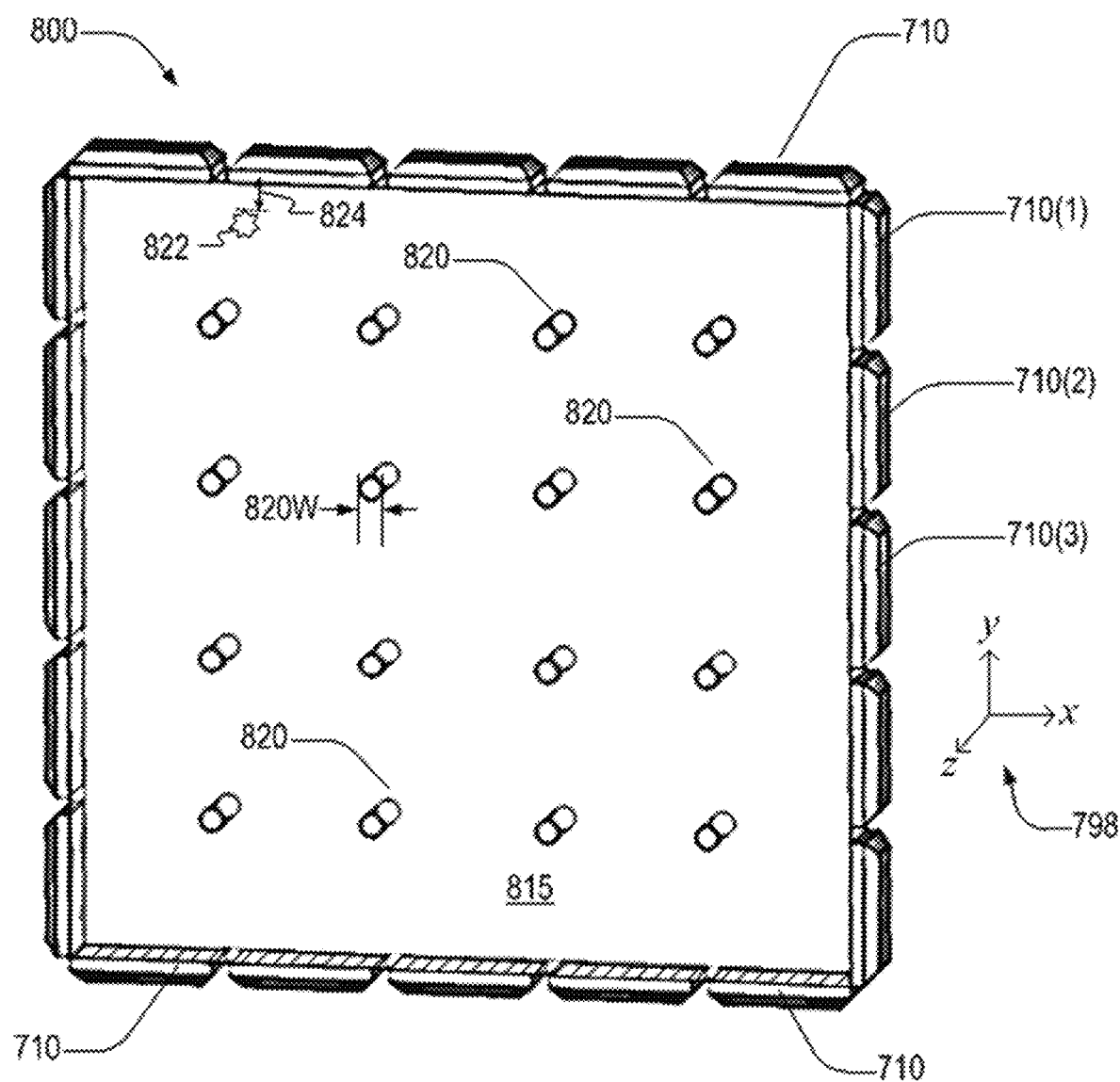
FIG. 8 shows an embodiment related to that of FIG. 7, but in which the scintillation detector has a plurality of optical scatterers.

FIG. 8 illustrates a graphical projection of a scintillation detector 800 that includes a scintillator substrate 815 and photodetectors 710. Scintillation detector 800 and scintillator substrate 815 are examples of scintillation detector 700 and scintillator substrate 715, respectively. Scintillator substrate 815 includes one or more optical scatterers 820. An optical scatterer 820 is anything that can reflect, refract, absorb or scatter photons that help to shape the MDRFs, including but not limited to a through hole or a blind hole drilled into the scintillator substrate 815, a laser-etched site, or a photon scatterer attached on the front and/or back surfaces of scintillator substrate 815. When optical scatterers 820 are configured as through holes or blind holes in the substrate, they may be optionally lined with a polymer coating, such as a fluoropolymer.

In the x-y plane as shown, one optical scatterer may have a cross-section having a closed shape. The closed shape is, for example, at least one of a conic section, a polygon, a concave shape, and a convex shape. Each optical scatter has a width 820W, which is 2.0±1.0 mm, for example. In an embodiment, each optical scatterer 820 is a cylindrical hole having a diameter 2.0±0.5 mm.

Scintillator substrate 815 may include at least one peripherally-located optical scatterer 822 with a distance 824 from an edge surface. In one embodiment, peripheral optical scatterers 822 are used to increase spatial resolution near the edges.

Figure 9:
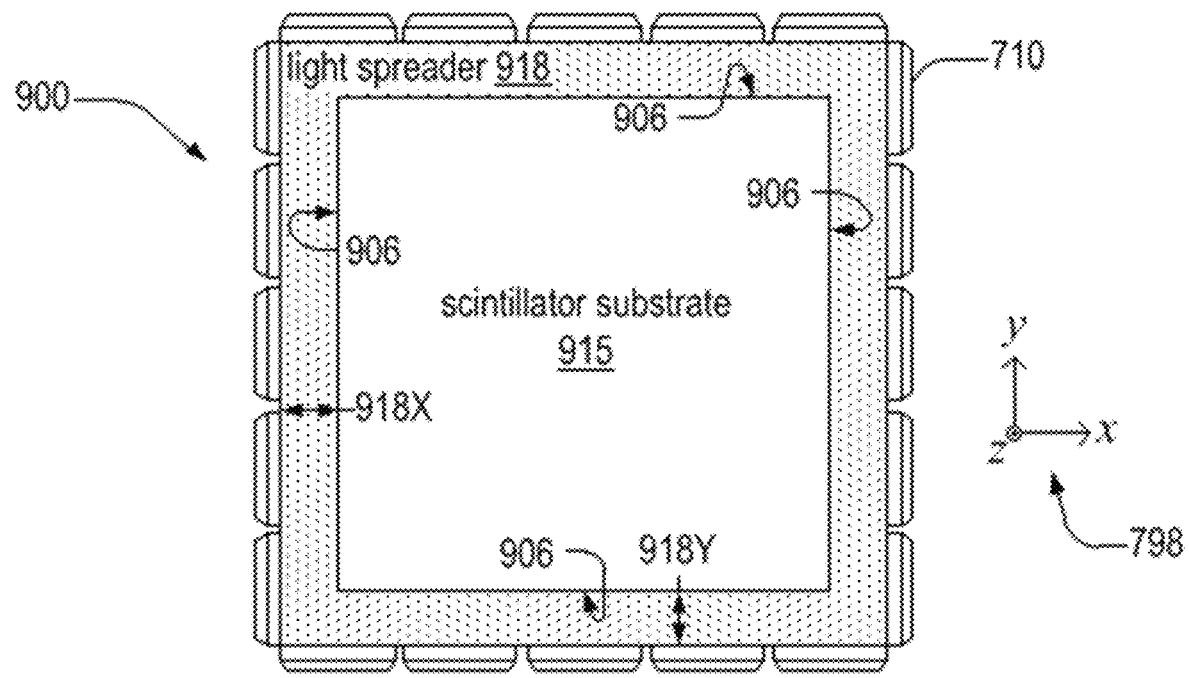
FIG. 9 depicts an embodiment of the invention according to which the scintillation detector includes a light spreader component.

FIG. 9 is a plan view of an embodiment of a scintillation detector 900, which includes a scintillator substrate 915, photodetectors 710, and a light spreader component 918. Scintillation detector 900 is an example of scintillation detector 700. Scintillator substrate 915 may be either scintillator substrate 715 or 815, and has edge surfaces 906, which are equivalent to edge surfaces 706 of scintillator substrate 715. Light spreader component 918 at least partially surrounds scintillator substrate 915 between edge surfaces 906 and detectors 710. Light spreader 918 may have a thickness, in the z direction, that is substantially equal to a distance between front surface 715F and back surface 715B at edge surface 706 of scintillator substrate 715. Light spreader 918 has thicknesses 918X and 918Y in the x direction and they directions. In an embodiment, the min and max of 918X and 918Y will depend on the size of the substrate 915, and typically will not exceed 0.25 W, where W is the width of the substrate 915 (if it is square). In an embodiment, the light spreader 918 comprises glasses, polymers or other transparent materials with good light-transmitting or optical coupling properties.

Due to the effect of total internal reflection (TIR) and the large difference of indeces of refraction between typical scintillator crystals ($n \gtrsim 1.8$) and air ($n=1$), if the front and back surfaces of the scintillation substrate are well polished, at least 83% of photons will be transported to the edges of the thin slab of the substrate with almost no loss. In an embodiment described herein, scintillator crystals with a lower refractive index of $n=1.1$ would still yield 41.6% of photons being transported to the edges of scintillator substrate 715.

Since photodetectors 710 (consider silicon photon multipliers (SiPMs) as an example of a photodetector below) are attached on edge surfaces 706, once the scintillation photons arrive at the edges, photodetectors 710 will absorb a portion of the scintillation photons and generate signals proportional to the number of photons absorbed. The summation of the signals gives the energy information (if the photodetectors are well calibrated), while the signal amplitude differences between different SiPMs give the position information. For example, if a gamma-ray photon interacts inside scintillator substrate 715 at a position close (e.g., closest) to photodetector 710(1), photodetector 710(1) will probably produce a relatively larger signal output compared with other photodetectors 710; this signal difference indicates that the interaction happened at a position close to photodetector 710(1).

A technical benefit of optical barriers/scatterers 820 is that such scatterers will cast shadows on photodetectors 710 by reflecting/deflecting the scintillation photons. The position of a shadow of a given optical barrier on a surface will move a significant distance even when the position of the is change only slightly with respect to one or more optical barriers 820. The significant shift of a shadow will produce a significant change of an amplitude of a signal generated by the photodetector 710 in the region where the shadow is cast. Thus, as a person of skill in the art will readily appreciate, the spatial resolution across the plane of the scintillator substrate 815 is greatly enhanced with the use of optical scatterers in the thin-slab substrate of a scintillation detector configured according to the idea of the present invention. In addition, since the photons are well confined within scintillator substrate 815, contrast of the shadows is significantly high, which means it is suitable to employ the thin slab edge readout technique when the optical scatterers 820 are present.

Figure 10:
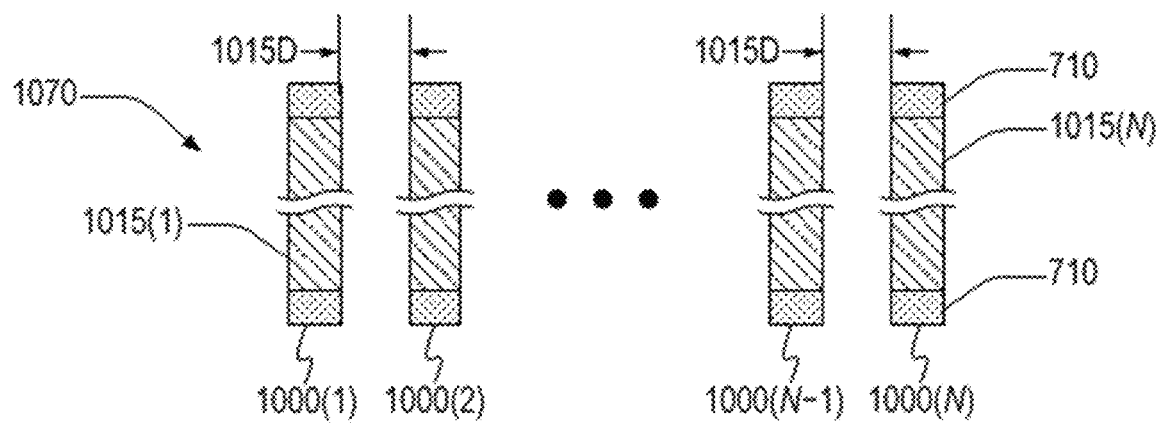
FIG. 10 is a cross-sectional view of a scintillation detector system that includes stacked scintillation detectors configured according to the idea of the invention.
Figure 11:
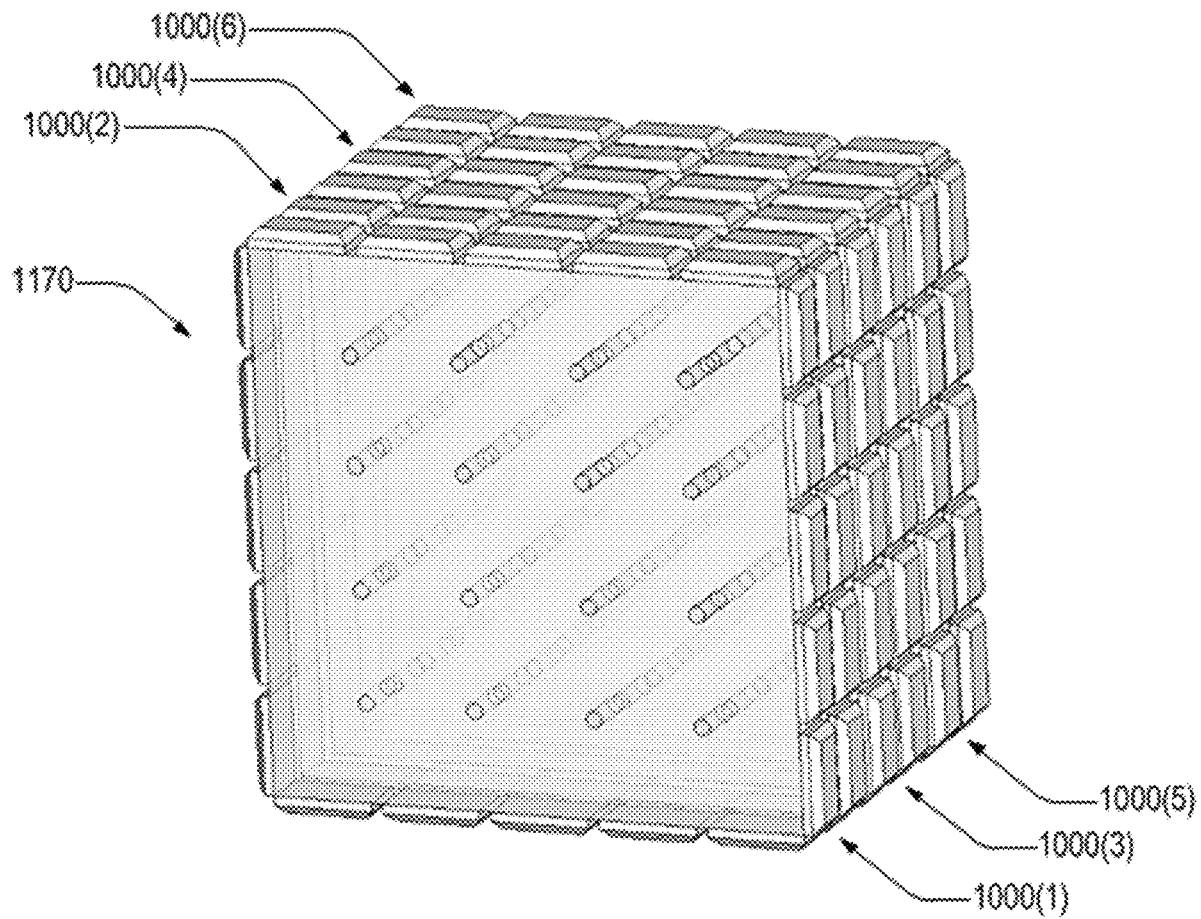
FIG. 11 is a perspective view of an embodiment of a stacked scintillation detector system.

FIG. 10 is a cross-sectional view of an embodiment of a scintillation detector system 1700 that includes a stack of constituent scintillation detectors 1000(1) through 1000(N), where N is a positive integer. Each scintillation detector 1000 is, for example, configured as a scintillation detector 700, and includes respective scintillator substrates 1015(1 . . . N), each of which can be configured as the scintillator substrate 715. Each individual scintillator substrate 1015 may be formed from a different scintillation crystal. For example, "odd" scintillation substrates 1015(1, 3, . . . ) may be formed from a first scintillation crystal and "even" scintillation substrates 1015(2, 4, . . . ) may be formed from a second scintillation crystal. FIG. 11 illustrates a graphical projection of a scintillation detector 1170, which is an example of scintillation detector 1070 with N=6. Immediately-neighboring constituent scintillator substrates 1015 are separated from one another by a distance 1015D (which may be between one millimeter and five millimeters, for example).

Embodiments of tacked scintillation detector systems 1070 and 1170 are capable of detecting more scintillation events than a single scintillation detector 1000. With the use of the embodiment 1070, 1170 for example, the determination of in which layer the gamma interaction occurs is possible This, in turn, provides information about the depth of interaction (DOI). Such capability, therefore, turns the embodiment 1070, 1170 into a 3D gamma-ray detector. Some readouts of the photodetector 710 used in the embodiment may be combined to decrease the total number of readouts without significantly affecting the result. Scintillation detector system 1170 is illustrated with six individual (constituent) scintillation detectors 1000 (that utilize approximately 10-20 mm plates of scintillation material) for illustrative purposes, but may include more or fewer individual scintillation detectors 700 without departing from the scope hereof.

Figure 12:
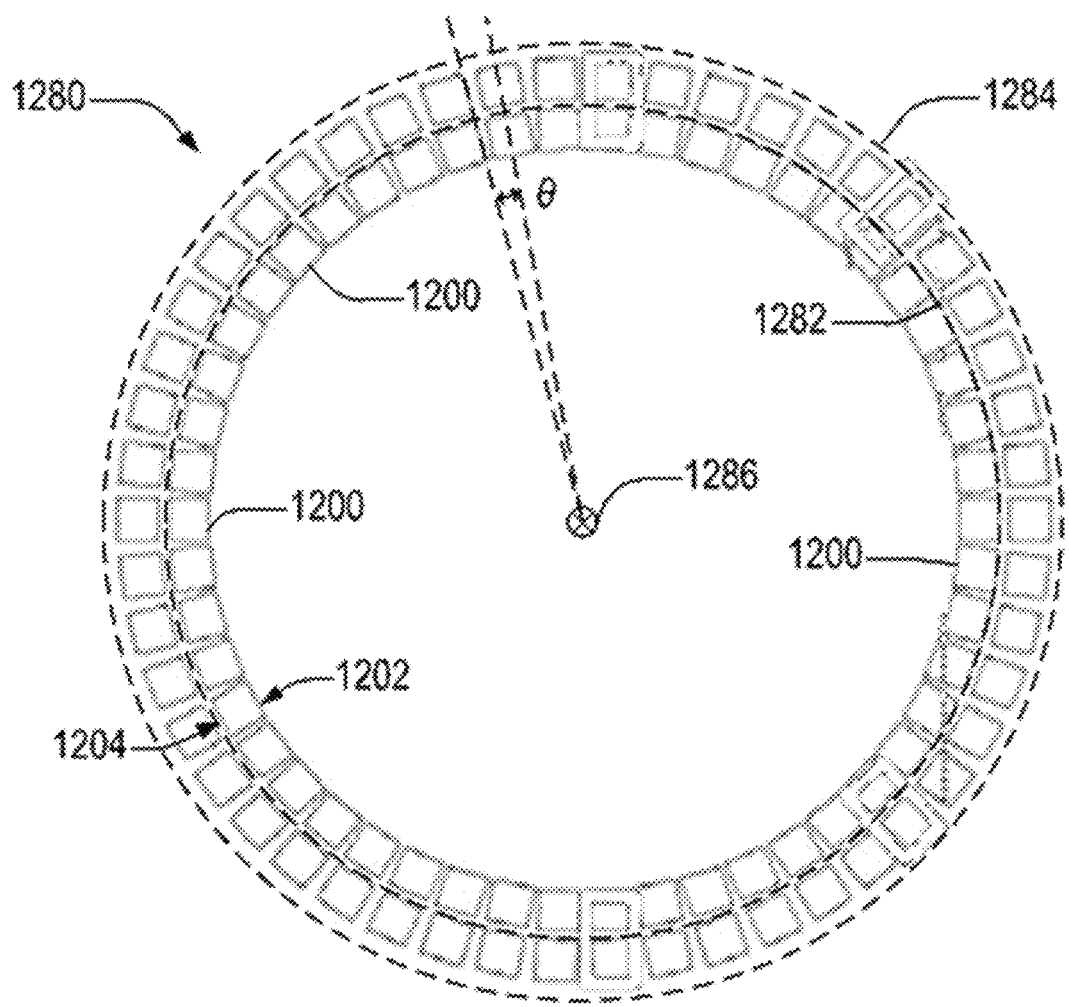
FIG. 12 shows an embodiment of a PET detector ring structured according to the idea of the invention.

FIG. 12 is a plan view of a PET detector ring 1280. PET detector ring 1280 includes a first plurality of scintillation detector systems 1200 arranged to form an inner ring-like shaped array of photodetectors within bounds of the dashed circle 1282. Each constituent scintillation detector system 1200 may be configured, for example, as an individual scintillation detector 700 or as a stacked scintillation detector system 1070, depending on the specifics of a particular implementation.

PET detector ring 1280 may also include a second plurality of scintillation detector system arranged to form an outer ring-like array (shown enclosed between dashed circles 1282 and 1284). Inner and outer rings (or ring-like arrays) may be coordinated to have a common center 1286. Scintillation detectors 1200 in the outer ring may be collectively rotated, if required, around the common center 1286 by an angle θ such that photons propagating through a gap between individual detector systems 1200 of the inner are impinging at a detector 1200 of the outer ring.

Each constituent scintillation detector system 1200 has a back surface 1204 opposite a front surface 1202. Surfaces 1202 and 1204 may correspond to, for example, the front surface 715F and back surface 715B of the scintillator substrate 715. Surfaces 1202 and 1204 may be planar and parallel to one another. Alternatively, surfaces 1202 and 1204 may be substantially cylindrical and, optionally, concentric with one another and, additionally or alternatively, have a common center of curvature on an axis drawn through the common center 1286 and normal to a plane of FIG. 12.

The discussed embodiments utilize thin slabs of scintillation crystals to acquire information about positions of each photon's interaction and energy; there is no need to pixelate the crystal (in contradistinction with related art), which provides solutions to problems summarized in sections on Limitations 2, 4, and 5 described in the Background of this disclosure. Stacking multiple substantially identically-structure layers of scintillation crystal slabs together increases detector stopping power, which in turn facilities determination of which layer the photon interaction occurs (direct readout), and the depth of interaction may be acquired. The depth of interaction resolution depends on the thickness of the scintillation crystal, which makes it easy to achieve a depth of interaction resolution of around one millimeter. Embodiments herein hence overcome limitation 3 described above. Moreover, the traditional pixelated detector has a chance to wrongly decode the pixels—mistakenly assigning an interaction event from a certain pixel to an adjacent pixel. By contrast, embodiments herein overcome this weakness since there is no need for pixel decoding. Additionally, embodiments of the present invention also do not contain pixel gaps, which results in increased gamma-ray sensitivity. In additional embodiments, the scintillation detectors of the present invention are used to detect scattering of photons by charged particles (i.e., Compton scattering).

Example 1

An analysis of side readouts of monolithic scintillation crystals. A method of using the side surfaces of a thin monolithic scintillation crystal for reading out scintillation photons is described. A Monte-Carlo simulation was carried out for an LYSO crystal of 50.8 mm×50.8 mm×3 mm with five silicon photomultipliers attached on each of the four side surfaces. With 511 keV gamma-rays, X-Y spatial resolution of 2.10 mm was predicted with an energy resolution of 9%. The addition of optical barriers was also explored to improve the X-Y spatial resolution. An X-Y spatial resolution of 786 μm was predicted with an energy resolution of 9.2%. Multiple layers may be stacked together and readout channels may be combined. Depth of interaction information (DOI) may be directly read out. This method provides an attractive detector module design for positron emission tomography (PET).

Figure 13:
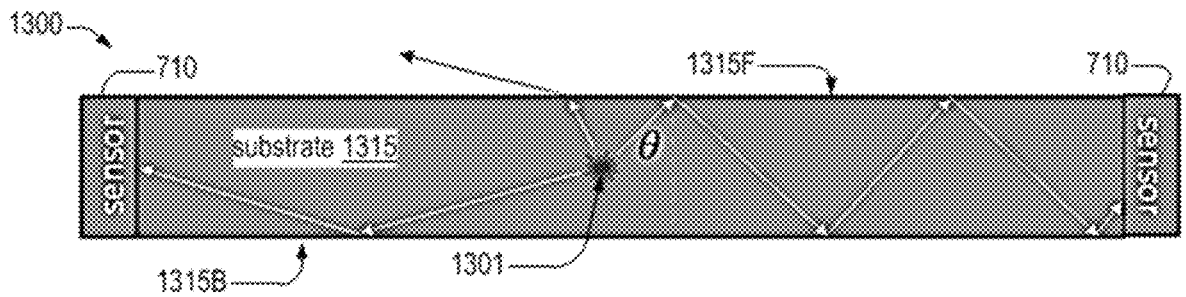
FIG. 13 provides a schematic illustration of total-internal reflection of a scintillation photon occurring in a slab of a scintillation crystal forming a monolithic substrate of an embodiment of a single scintillation detector.

FIG. 13 illustrates a scintillation event 1301 (or equivalently, a gamma-ray interaction event) within scintillator substrate 1315 of a scintillation detector 1300. Scintillator substrate 1315 has a high refractive index, e.g., exceeding 1.7, compared to its surrounding medium, e.g., air. Scintillator substrate 1315 is, for example, one of scintillator substrates 715, 815 and 915. Similarly, scintillation detector 1300 is, for example, one of scintillation detectors 700, 800, and 900.

If substrate 1315 has no surface coatings, most of the scintillation photons will be reflected by top surface 1315F and back surface 1315B due to total internal reflection (TIR). Only a small portion of scintillation photons with incident angles smaller than a critical angle $\theta_c$ have a chance to escape. For the LYSO crystal surrounded by a medium with unity refractive index, $\theta_c$=33.8° at the gamma-ray frequencies of interest. The majority (>80%) of the photons will impinge on the front and back surfaces with angles larger than the critical angle, and will propagate, via TIR, to the edges of the scintillator.

In these simulations, the photons reaching the four thin sides are collected by photon sensors attached to them. The information in the amplitudes of the photon sensor signals allows the position and energy information of the gamma-ray to be estimated.

Figure 14:
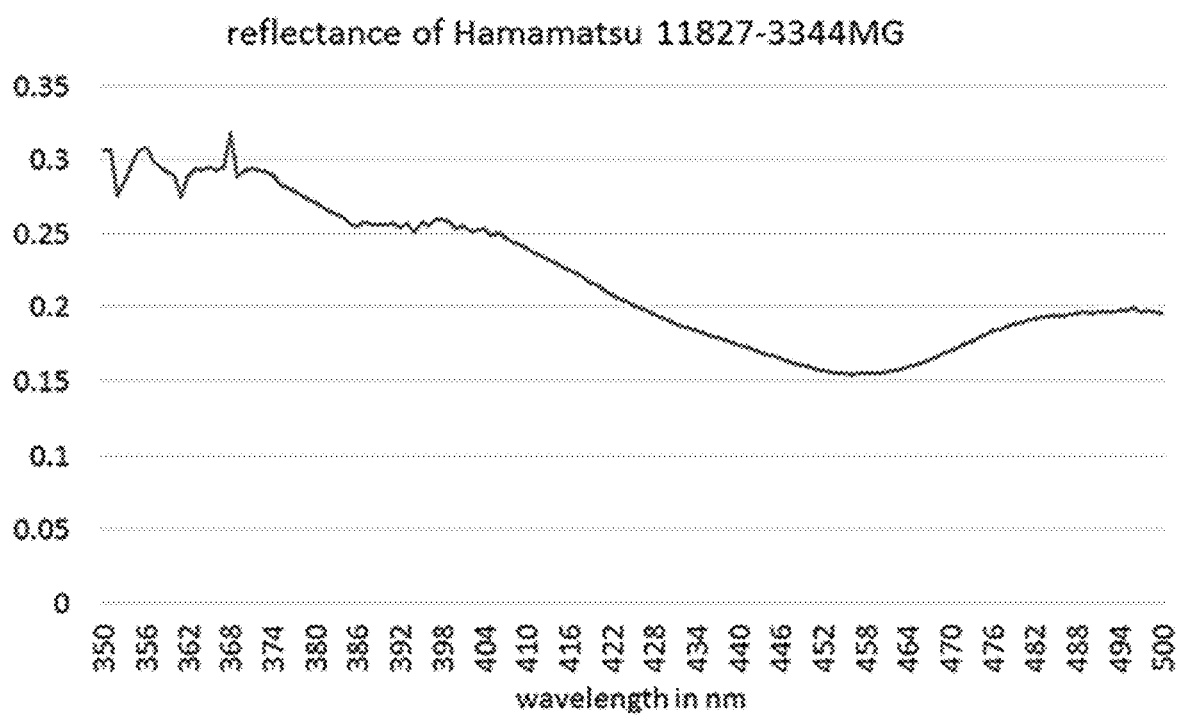
FIG. 14 shows a spectral reflectance curve of a typical silicon photomultiplier.
Figure 15:
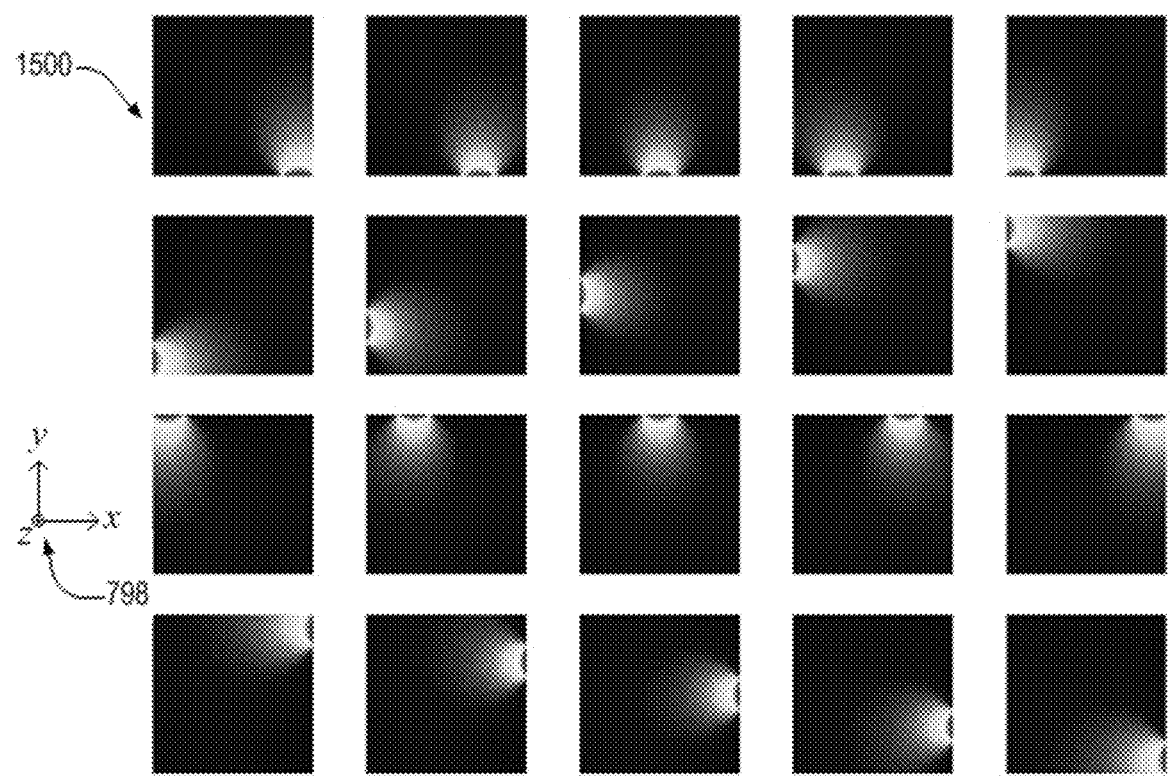
FIG. 15 shows images of simulated mean detector response functions (MDRFs) of a thin layer detector formed of lutetium-yttrium oxyorthosilicate (LYSO).
Figure 16:
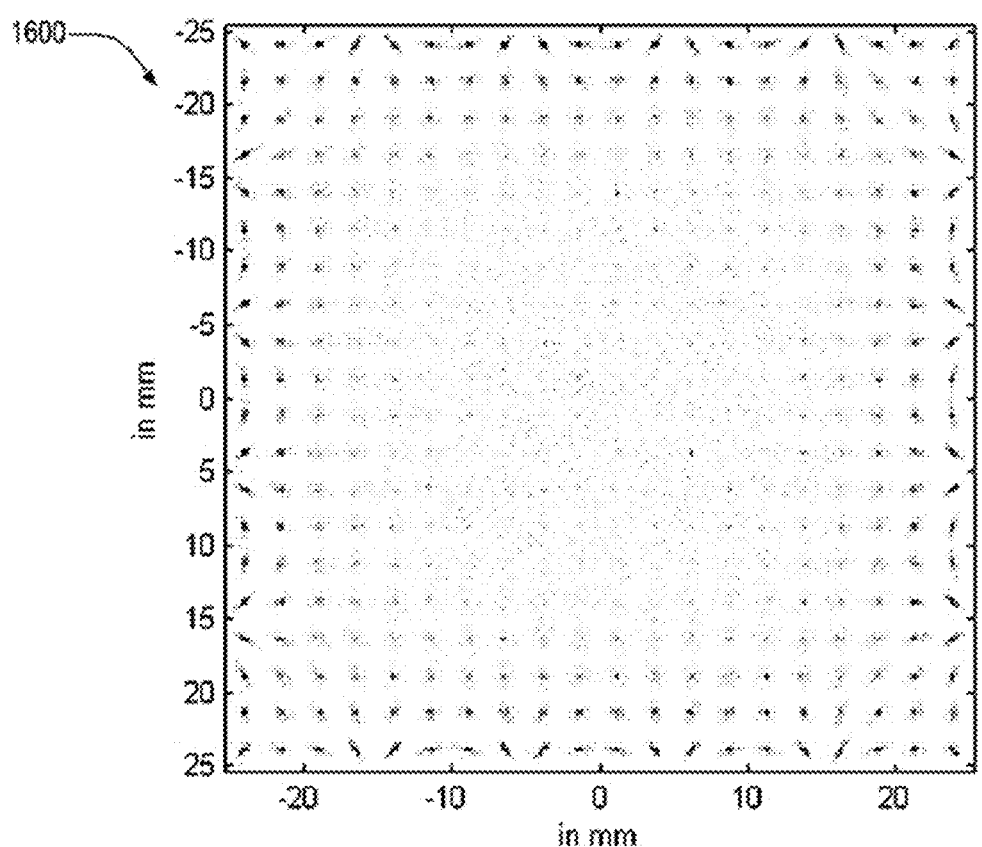
FIG. 16 is a plot of an estimated interaction position derived from the MDRFs of FIG. 15. Positions corresponding to the central portion of the plot cannot be resolved due to poor resolution.

FIGS. 15 and 16 illustrate results of a Monte Carlo simulation of scintillation substrate 700. The simulation was in part based on spectral reflectance of a spectrometer shown in FIG. 14, as described below. The simulated scintillator substrate was a 50.8-mm×50.8-mm LYSO slab, with thickness of three millimeters. Five silicon photomultipliers (SiPM) are attached on each side surface of the thin slab, so there are a total of twenty SiPMs. The spectrum-averaged photon detection efficiency (PDE) was chosen to be 20%. The dark current rate was chosen as 1.0 MHz/mm$^2$, the excess noise factor (ENF) of the SiPMs was assumed to be 1.21. These parameters were chosen conservatively, within the limits of performance parameters provided by several manufacturers.

A portion of the photons that arrive at the side surfaces of the scintillation crystal will be reflected due to the refractive index differences of the SiPM's window material, silicon substrate, optical gel, and scintillation crystal. The reflected photons are deleterious to the interaction-position estimation. To measure the reflectance of SiPM, Hamamatsu 11827-3344MG was scanned in a Cary 5000 spectrometer. The spectral reflectance curve is shown in FIG. 14. The reflectance in the simulation was chosen to be 0.4 as a conservative estimate, and the type of reflection was chosen to be specular reflection.

The mean-detector-response function (MDRF) was acquired by simulating a scan of a 511 keV gamma-ray beam normal to the LYSO scintillator surface in a matrix of 252×252 points across the 50.8 mm×50.8 mm scintillator area (depth=3.0 mm), with a step size of 0.2 mm. FIG. 15 illustrates the simulated MDRF, MDRF 1500, which includes twenty 50.8-mm×50.8-mm frames. Each frame corresponds to one of twenty SiPMs each attached to one of the four sides of the detector.

The mean-detector-response function (MDRF) is used to find the gamma-ray interaction position and energy with maximum likelihood estimation. If the detector is sampled by a tightly collimated beam, at positions of a 20×20 square array having 2.5-mm spacing for example, the estimated interaction positions are shown in point-grid image 1600, FIG. 16. Point-grid image 1600 may be derived from MDRF 1500 using a maximum-likelihood estimation (Hesterman, Jacob Y. et al. "Maximum-Likelihood Estimation With a Contracting-Grid Search Algorithm." *IEEE Transactions on Nuclear Science* 57.3 (2010): 1077-1084).

The average spatial resolution of the points in point-grid image 1600 as defined by FWHM is 1.49 mm, and the average absolute values of biases in x, y directions are 56 μm and 52 μm, respectively. However, points near the plane center cannot be resolved. As used in this context, "bias" refers to the difference between true positions and estimated positions averaged over many events at different positions on the detector plane.

The energy resolution of this detector is given by equation.

$$\left(\frac{\Delta E}{E}\right)^2 = (\delta_{sc})^2 + (\delta_p)^2 + (\delta_{st})^2 + (\delta_n)^2.$$

The symbol δ represents the 2.355 times the standard deviation of each component normalized by the estimated energy in unit of photon number. $\delta_{sc}$ is the intrinsic resolution of the scintillation crystal, $\delta_p$ is the transfer resolution, $\delta_{st}$ is the statistical resolution and $\delta_n$ is the energy deviation caused by dark current rate. For this simulation, $\delta_{sc} \approx 7.8\%$, $\delta_p \approx 0.91\%$, since the MDRF is quite uniform, $$\delta_{st} = 2.35 \times \sqrt{\frac{ENF}{N}} \approx 4.1\%, \delta_n \approx 1.43\%, \left(\frac{\Delta E}{E}\right) \approx 9.0\%,$$

and ENF denotes the excess noise factor.

Figure 17:
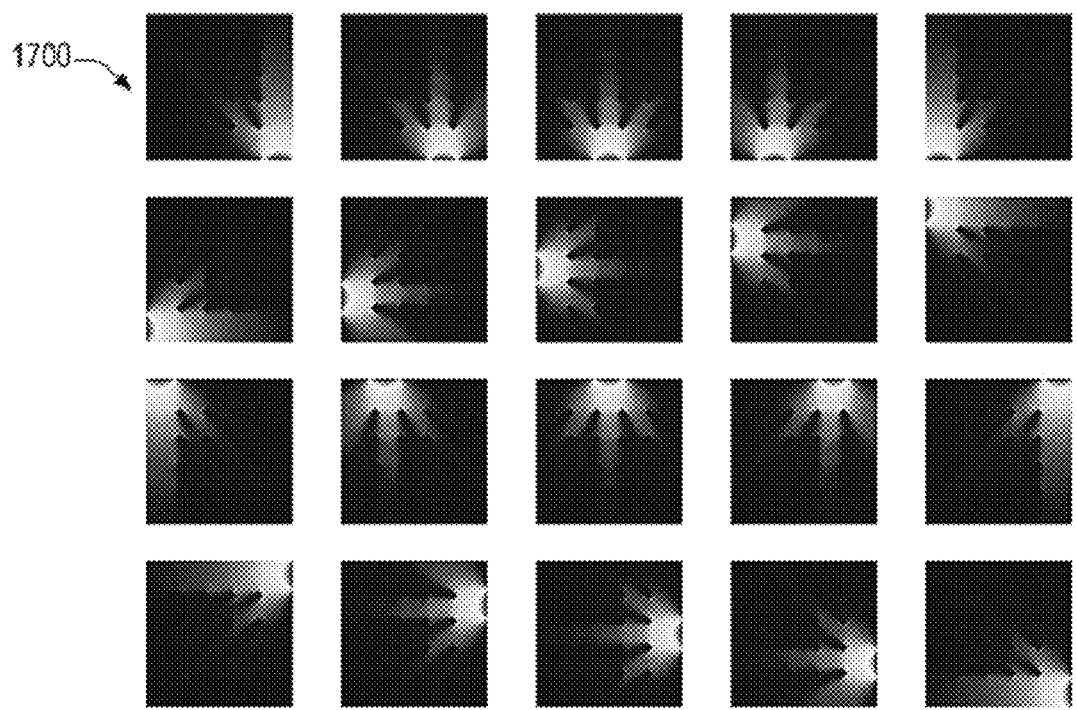
FIG. 17 illustrates simulated MDRFs of a thin layer LYSO detector with optical barriers/scatterers built-in into an embodiment of a detector structured according to one embodiment of the invention. The shadows produced by the optical scatterers can be seen to reshape the MDRF.

Optical barriers 820 (also referred to herein as optical scatterers) may be introduced to improve interaction position estimation. They may be holes mechanically drilled through the scintillator, photon absorbers or scatterers attached on the two major surfaces (for breaking the TIR condition) or even laser-etched patterns. Shadows will be created due to the block or redirection of scintillation photons. Optical barriers created in the plane of the crystal layer, may result in improved spatial resolution. For example, adding 16-square 2-mm Lambertian rods of reflectance 0.95 inside the crystal layer in a 4×4 grid results in a modified MDRF 1700, shown in FIG. 17.

Figure 18:
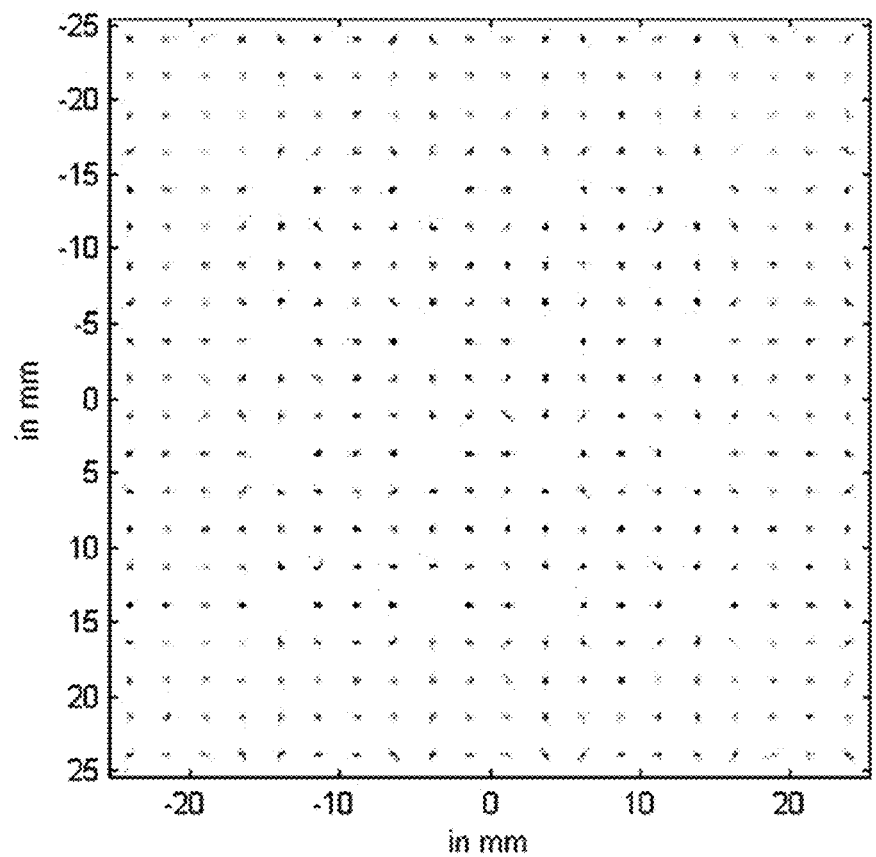
FIG. 18 is a plot of an estimated interaction position derived from the MDRFs of FIG. 17. Here, in advantageous contradistinction with the result of FIG. 16, positions corresponding to the central portion of the plot are spatially resolved due to improved spatial resolution provided by an embodiment of the invention.

As shown in FIG. 18, the modified MDRF yields improved spatial resolution, at a cost of reduced sensitivity due to inclusion of the rods (about 2.48% reduction). The average spatial resolution is 786 μm, the average absolute values of biases in X, Y directions are 23 μm and 22 μm, respectively, and ΔE/E≈9.2%. The energy resolution is worse than that without barriers, due to the photon loss and unevenness caused by the rod barriers.

Figure 19:
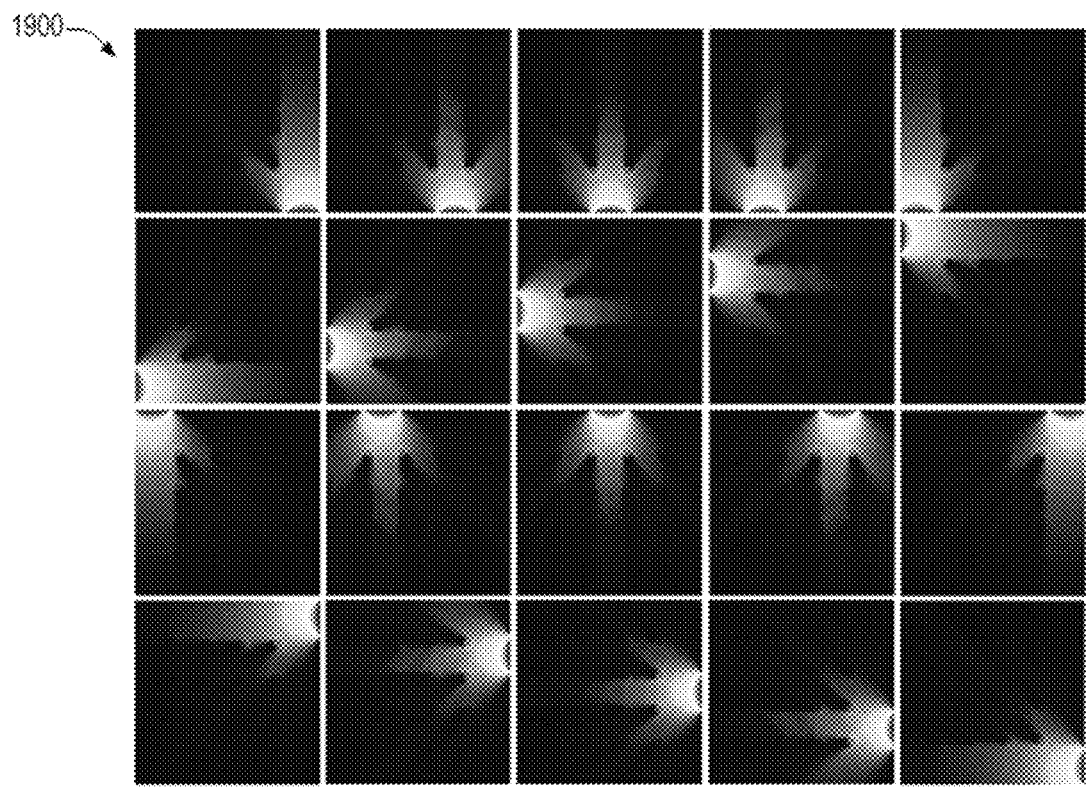
FIG. 19 illustrates simulated MDRFs of a thin layer LYSO detector with laser-etched (or laser engraved) optical barriers/scatterers in one embodiment of the invention.
Figure 20:
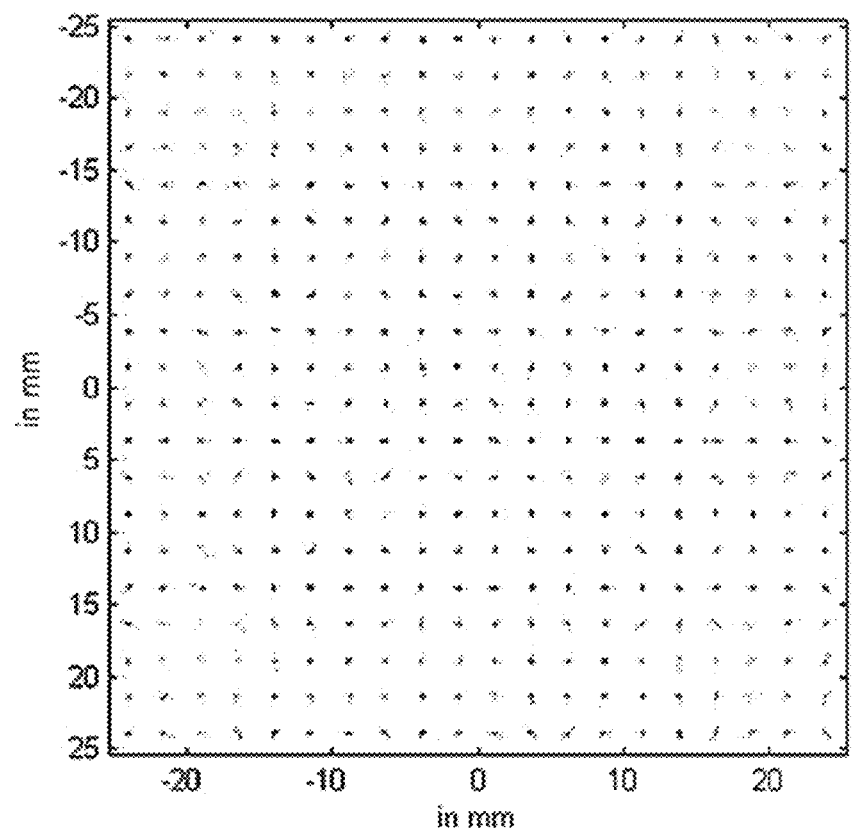
FIG. 20 shows an estimated interaction position derived from the MDRFs of FIG. 19.

Laser etching may create Lambertian surfaces to form the optical barrier pattern. For example, a 4×4 grid of 2-mm diameter rods may be created inside the crystal layer, at the same positions of FIG. 17, resulting in an MDRF 1900, FIG. 19. As shown in FIG. 19, there is no dead area compared with FIG. 17, so gamma-ray interaction positions within the rod areas may be determined. The interaction-position estimations of 20×20 scan is shown in FIG. 20. The laser-etched barrier yields an improved average spatial resolution of 867 μm, the average absolute values of biases in x, y directions are 30 μm and 33 μm, respectively, ΔE/E≈9.4%.

Figure 21:
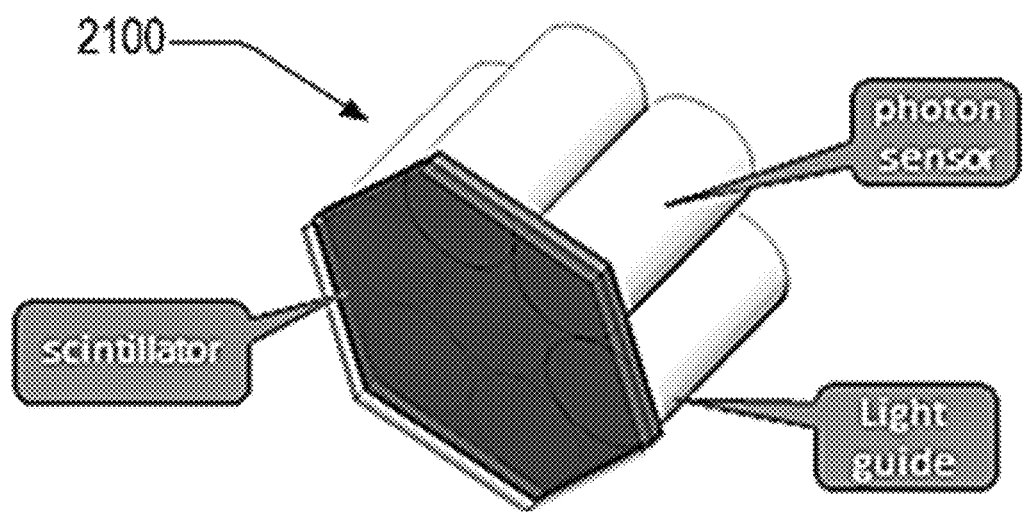
FIG. 21 and FIG. 22 depict, respectively, a conventional modular detector and a conventional pixelated detector employed in related art.
Figure 22:
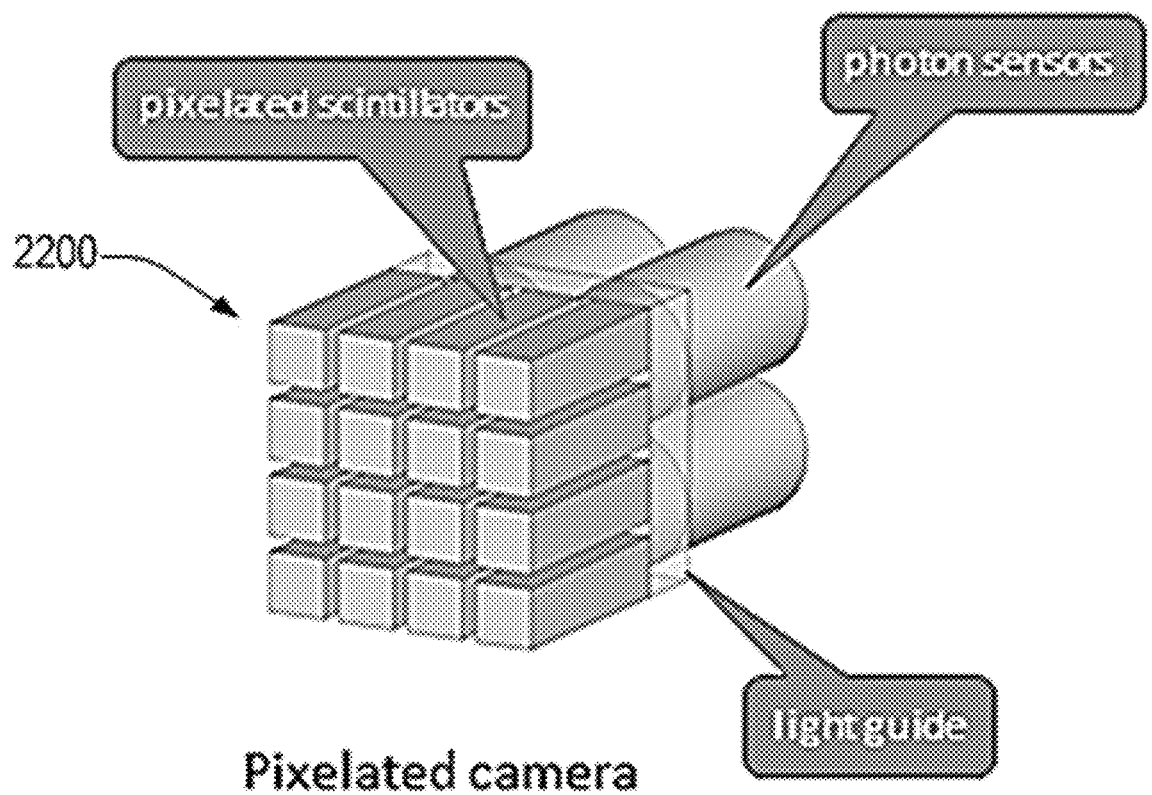

FIG. 21 and FIG. 22 depict, respectively, a conventional modular detector 2100 and a pixelated detector 2200. These conventional detectors have several significant limitations. For example, the crystal layers in traditional modular cameras have a finite thickness, which results in lower detection efficiency for higher energy rays. Additionally, it is hard to make calibrations for depth of interaction (DOI). X-Y resolution is coupled with DOI position and is usually biased at edges or corners. Pixelated detector modules, such as used in PET detectors, typically have higher cost for cutting and treating crystal surfaces and making arrays of small pixelated crystals can be very challenging. Additionally, it is complicated to achieve DOI information and there is a loss of sensitivity due to the gaps between pixels.

Figure 23:
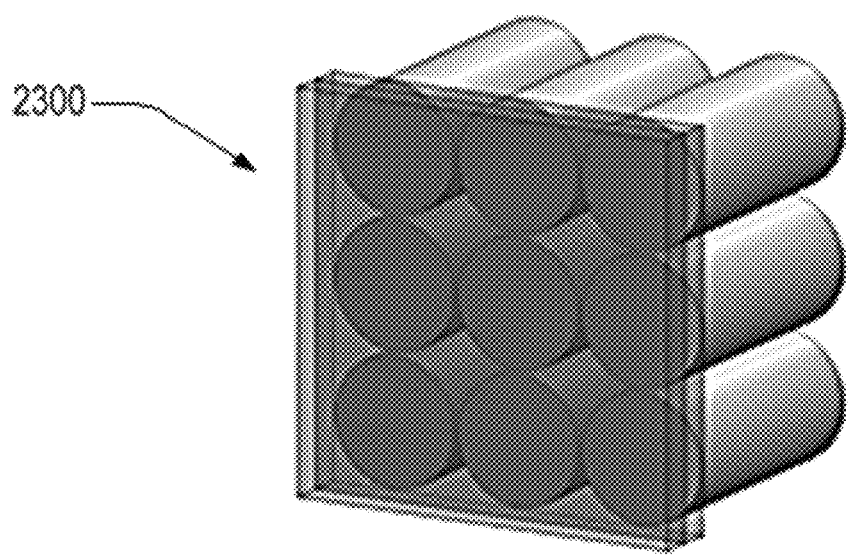
FIG. 23 and FIG. 24 illustrate a detector package where the scintillation detector comprises a slab substrate with the photon sensors positioned behind the back of the scintillator and light-guide substrate surface instead of the side edges.
Figure 24:
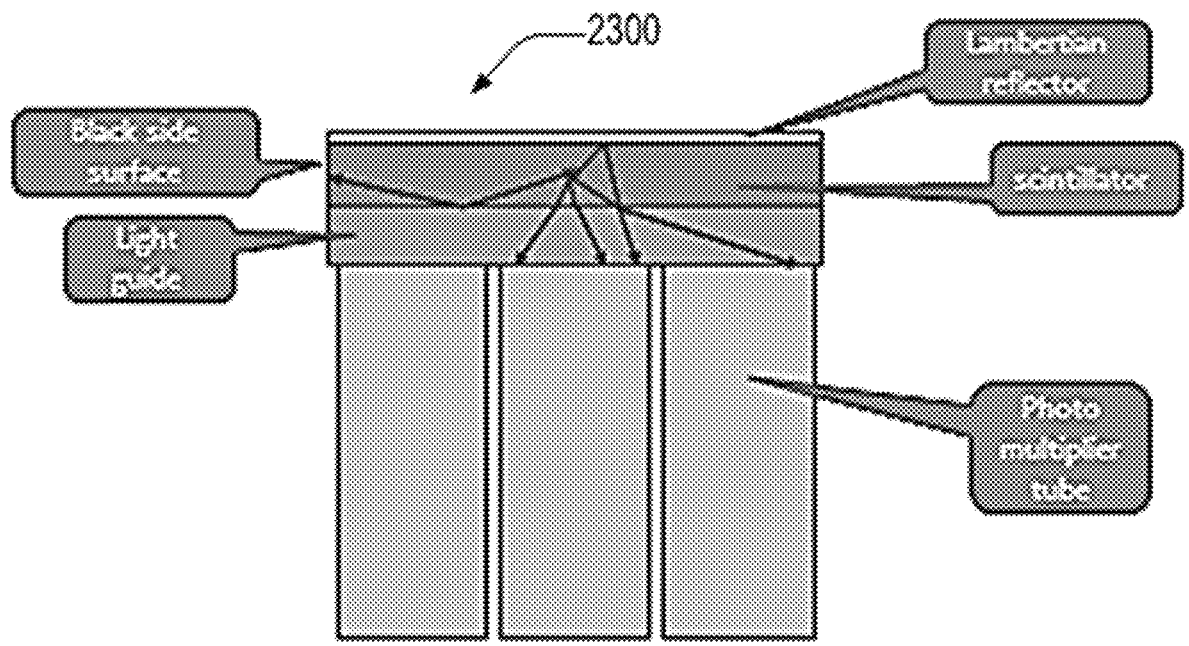
Figure 25:
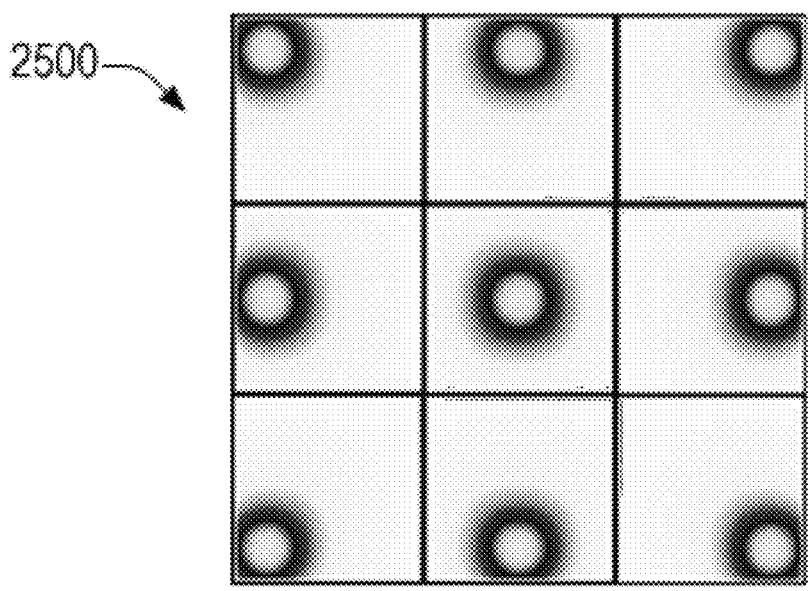
FIGS. 25 and 26 illustrate, respectively, MDRFs and interaction-position estimates of the detector package of FIG. 23.
Figure 26:
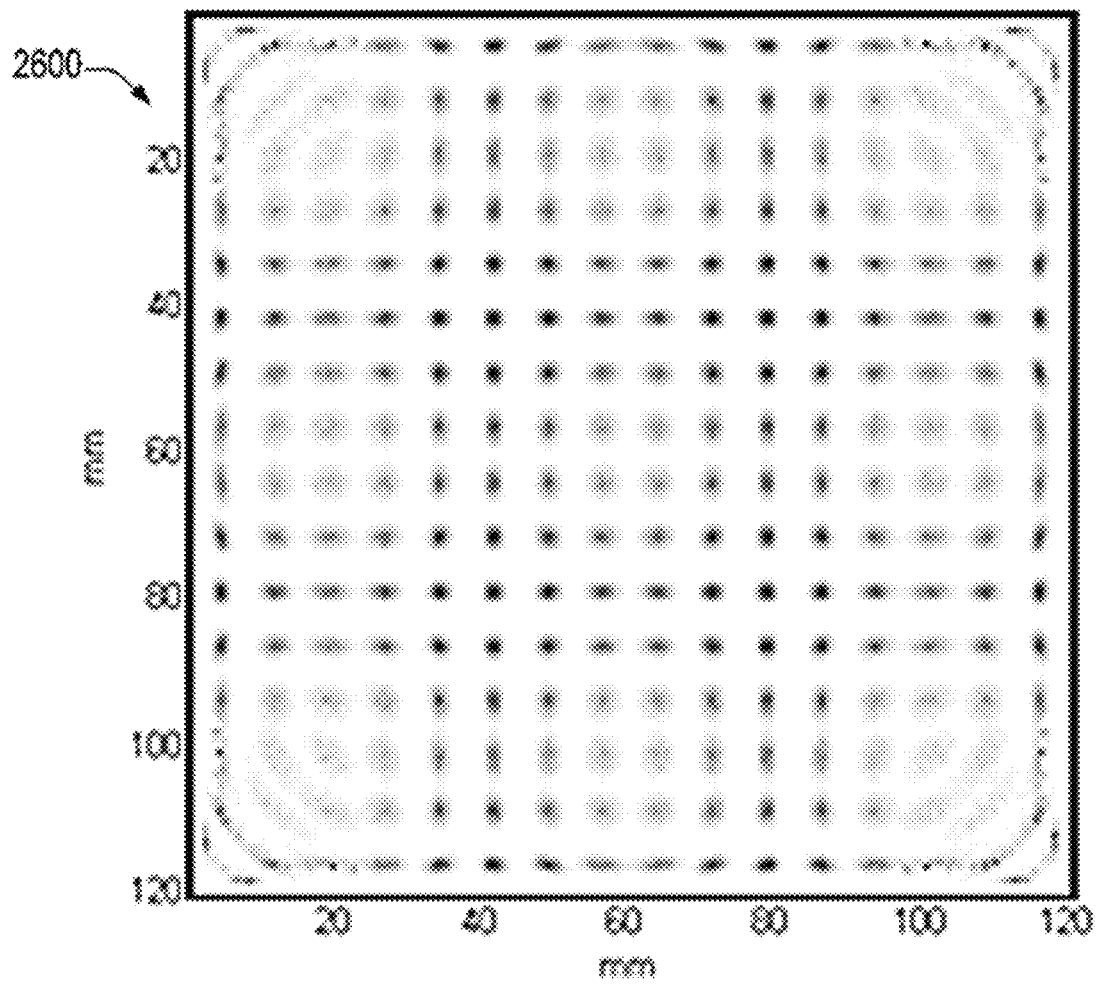

However, the improved performance of the present invention is not due to just the use of a slab of scintillation material. Positioning the photon sensors along the edges of the scintillation detectors provides additional benefits. FIG. 23 and FIG. 24 are schematics of detector package 2300 where the scintillation detector comprises a slab substrate with the photon sensors positioned behind the back substrate surface. This configuration results in MDRF 2500, FIG. 25, and point-grid image 2600, FIG. 26. FIGS. 23-26 illustrate that the positioning seen in a monolithic crystal detector is relatively poorer due to a larger point spread function. Additionally, the positioning at the center of each PMT degrades (cannot be resolved), and the positioning close to detector edges has poorer spatial resolution.

Figure 27:
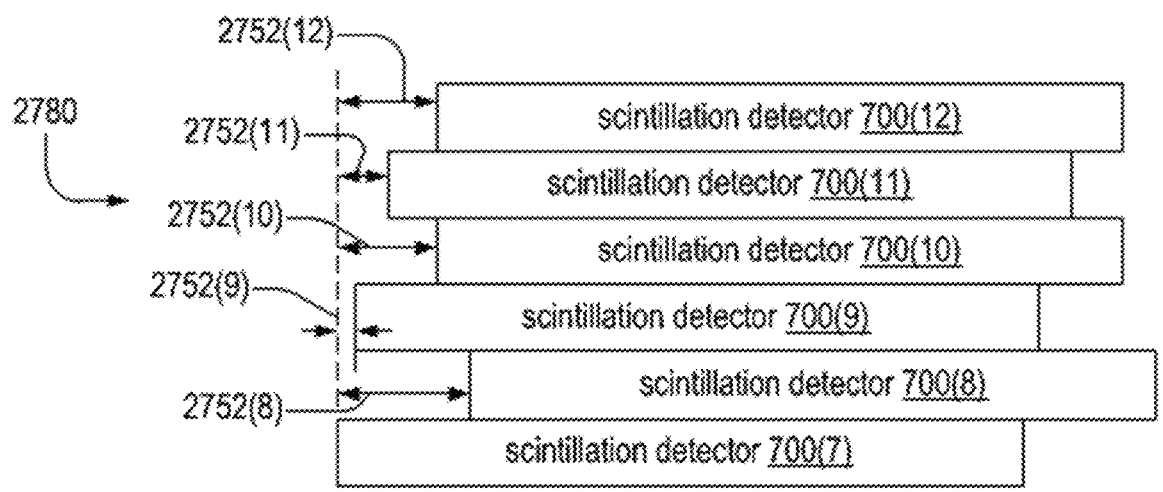
FIG. 27 and FIG. 28 illustrate cross-sectional views of embodiments of stacked scintillation detectors configured according to the idea of the present invention, where the scintillation detectors of each stack are laterally offset from one another.

FIG. 27 illustrates a stacked scintillation detector 2780, which includes a stack of scintillation detectors 700(7-12). Scintillation detectors 700(8-12) are horizontally offset from scintillation detector 700(7) by respective distances 2752(8-12). Any two distances 2752 may be equal.

Figure 28:
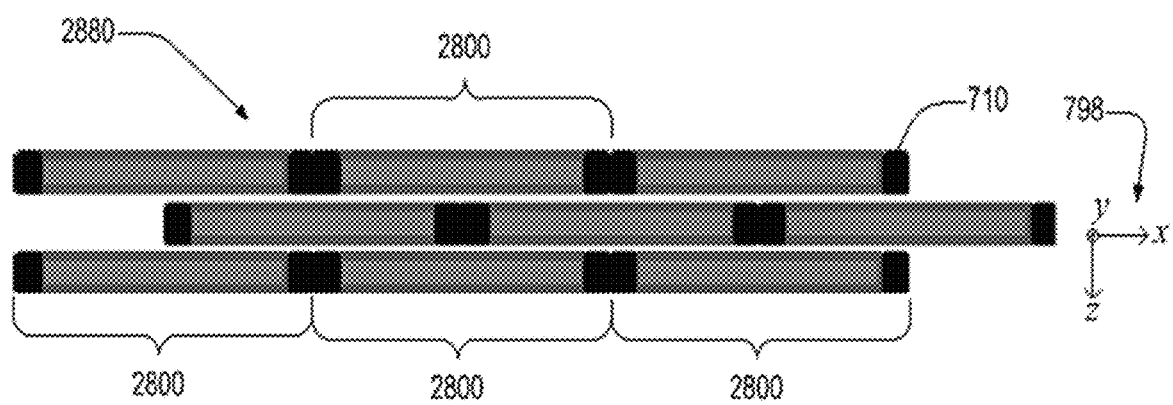

FIG. 28 illustrates a stacked scintillation sensor 2880 that includes a plurality of scintillation detectors 2800, which are each examples of scintillation detector 700. Scintillation detectors 2800 are stacked in the z direction. As shown in FIG. 28, the scintillation detectors 2800 in each row are laterally offset, in the x direction, to scintillation detectors in a different row. Each scintillation detector 2880 includes a plurality of photodetectors 710.

FIG. 29 illustrates a stacked scintillation sensor 2980A that includes a plurality of scintillation detectors 2900 in two curved rows 2983 and 2984. Each scintillation detector 2900 is an example of scintillation detector 700. Each scintillation detector 2900 includes a plurality of photodetectors 710. Each scintillation detector 2900 has a front surface 2902 and a back surface 2904, which in this example have the same respective concavity. Each photodetectors 710 in each row (e.g., row 2983) are aligned to a respective photodetector 710 in a different row (e.g., row 2984). For example, photodetector 710(291) is aligned with photodetector 710 (292).

FIG. 30 illustrates a stacked scintillation sensor 3080 that includes a plurality of scintillation detectors 3000 in two curved rows 3083 and 3084. Scintillation detectors 3000 in row 3083 are laterally offset from scintillation detectors 3000 in row 3084 relative to an axis perpendicular to the front substrate-surfaces of the first scintillation detector (not shown).

FIG. 31 illustrates a stacked scintillation sensor 3175 that includes a plurality of scintillation detectors 3100 in three curved or angled rows 3181-3183. Each scintillation detector 3100 includes a plurality of photodetectors 710 surrounding a scintillator substrate 3115. Scintillator substrate 3115 is an example of a scintillator substrate 715, and has a trapezoidal cross-section, which facilitates orienting adjacent scintillation detectors 3100 in a same row. Scintillator substrate 3115 has a front surface 3115F and a back surface 3115B, which are planar in the embodiment of FIG. 31.

Figure 32:
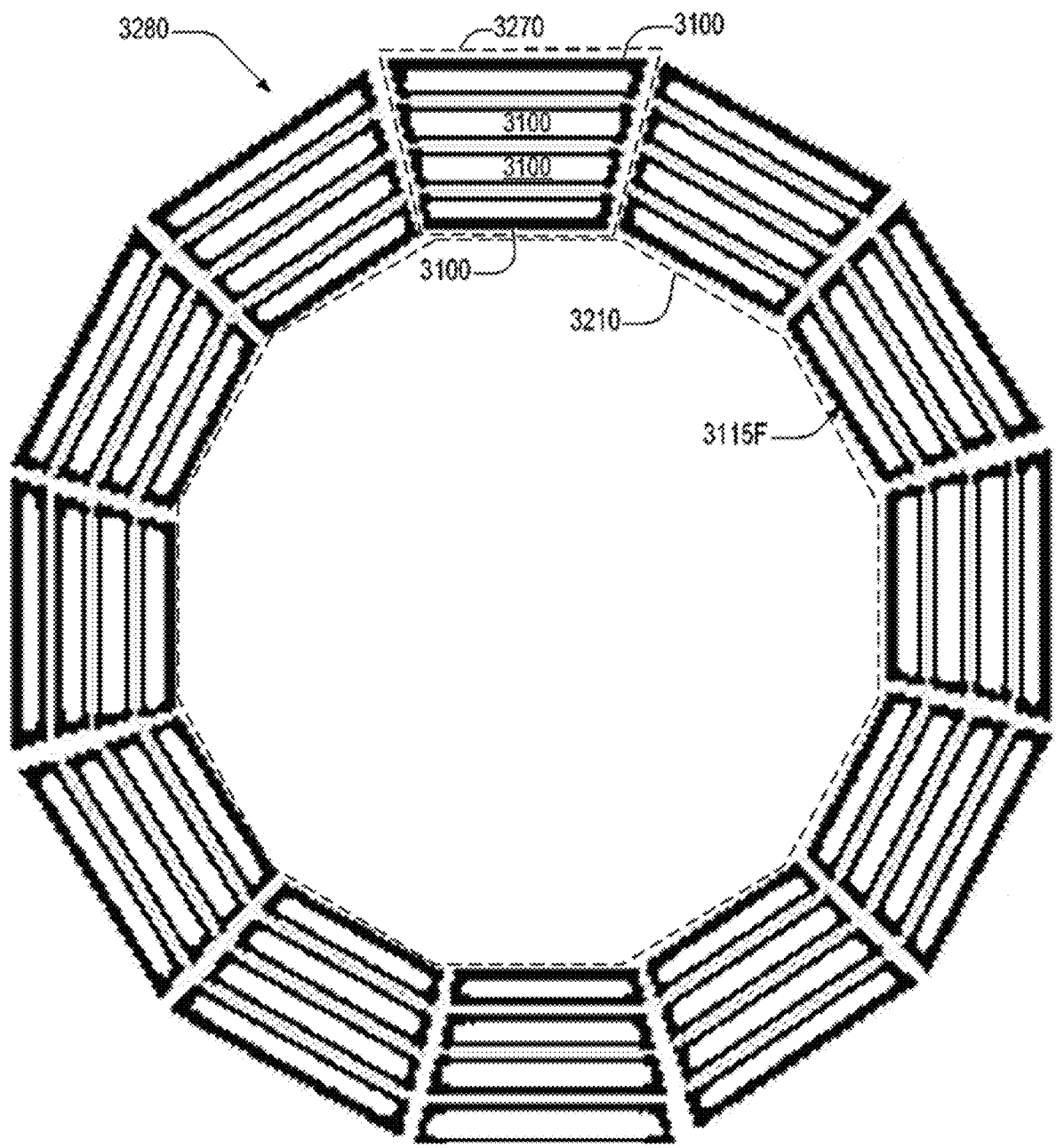
FIG. 32 is a plan view of twelve stacked scintillation detectors arranged to form a PET detector ring, in an embodiment.
Figure 33A:
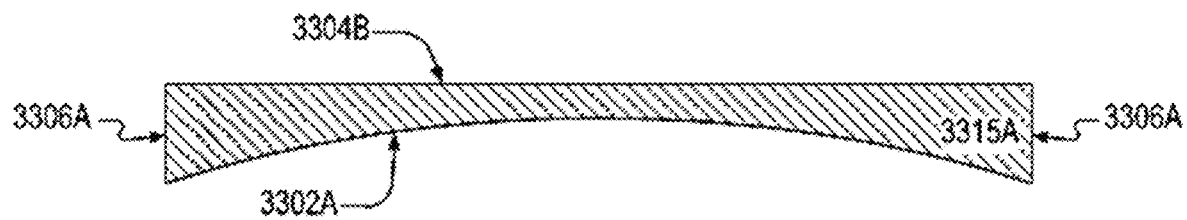
FIGS. 33A, 33B, 33C, 33D, and 33E illustrate cross-sectional views of scintillation substrates having different shapes and surface curvatures, in respective embodiments.
Figure 33B:
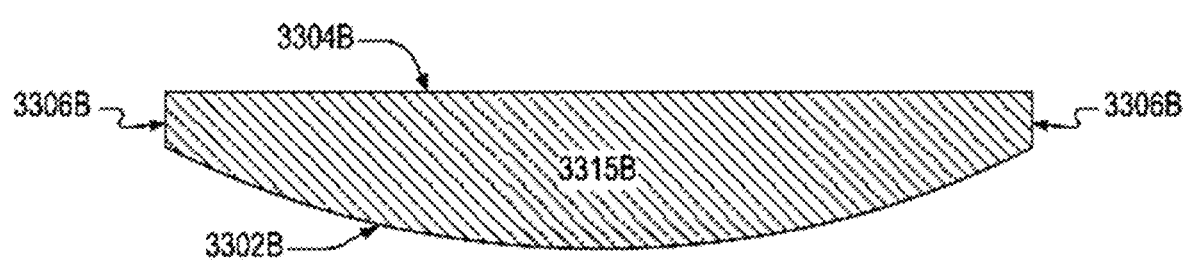
Figure 33C:
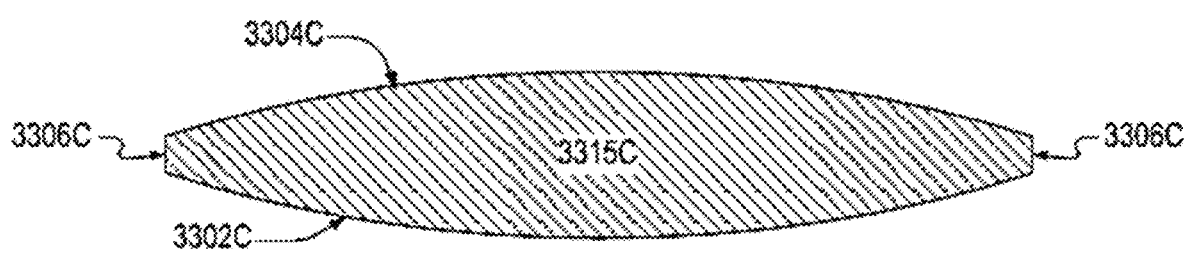
Figure 33D:
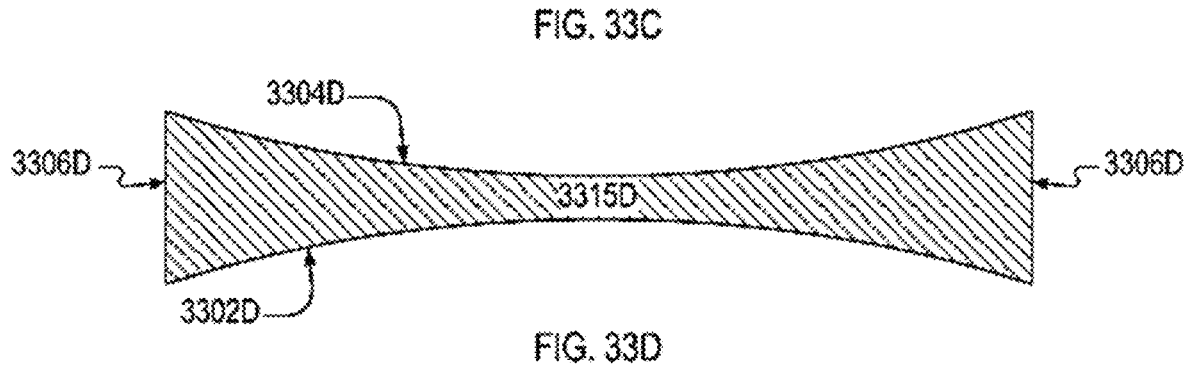
Figure 33E:
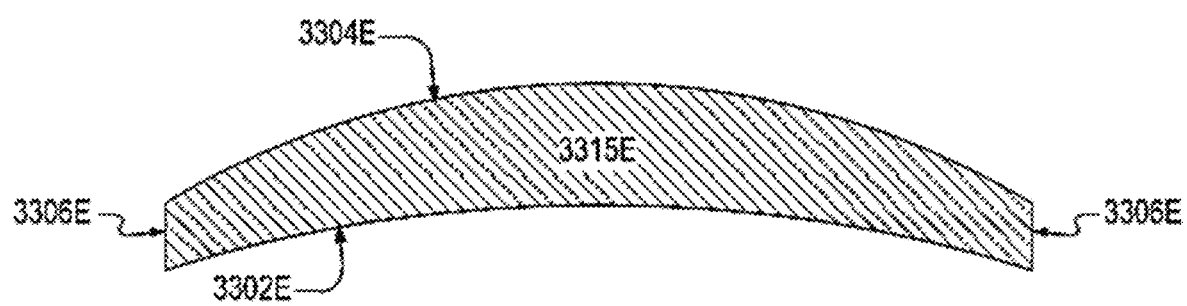

FIG. 32 is a plan view of twelve stacked scintillation detectors 3270 arranged to form a PET detector ring 3280. Each stacked scintillation detector 3270 includes four scintillation detectors 3100, and is an example of stacked scintillation detector 1170, FIG. 11. Stacked scintillation detectors 3270 are arranged to form a aperture 3210 defined by twelve front surfaces 3115F of inner-most scintillation detectors 3100. When surfaces 3115F are planar, aperture 3210 is a polygonal aperture. Without departing from the scope hereof, PET detector ring 3280 may include fewer than or more than twelve stacked scintillation detectors 3270.

FIGS. 33A-E are cross-sectional views of different possible scintillation substrates 3315A-3315E, which are example of scintillation substrate 715. Each scintillation substrate 3315 has opposing surfaces 3302 and 3304, which independently from one another may be planar, concave, or convex. Each scintillation substrate 3315 has edge surfaces 3306, which are in optical communication with photodetectors 710 when a scintillation substrate 3315 is part of a scintillation detector 700. It is understood that FIGS. 33A-E are non-limiting examples and that scintillation substrates having different or modified cross-sections are also suitable and encompassed by the present invention.

Figure 34:
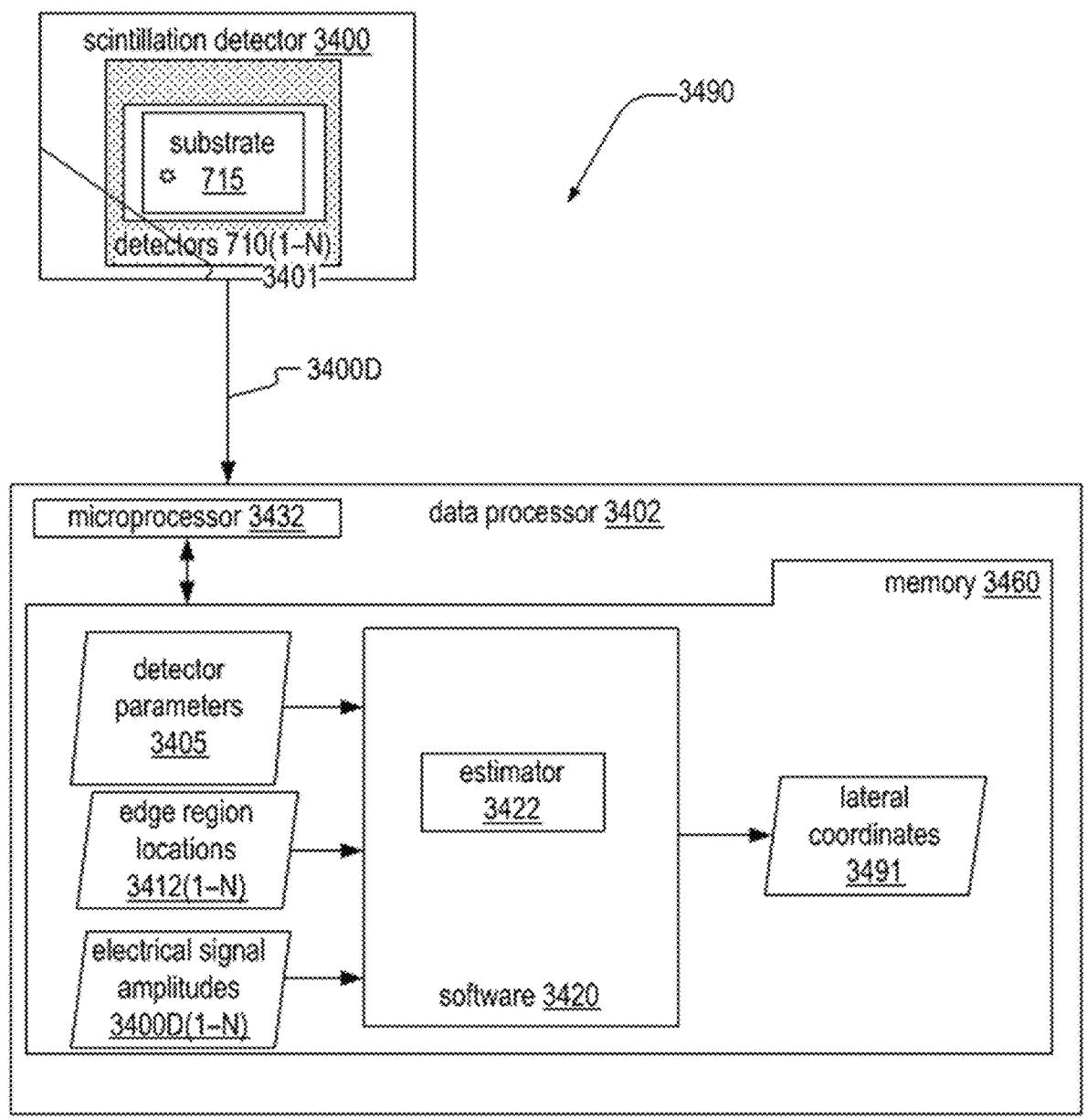
FIG. 34 is a schematic block diagram of an embodiment of a PET scanner configured to operate with one or more scintillator detectors disclosed in reference to of FIGS. 7 through 11.

FIG. 34 is a schematic block diagram of a PET scanner 3490. PET scanner 3490 includes a scintillation detector 3400 communicatively coupled to a data processor 3402. Data processor 3402 includes a microprocessor 3432 communicatively coupled to a memory 3460, which stores software 3420. Microprocessor 3432 performs functions of PET scanner 3490 described herein when executing machine-readable instructions of software 3420.

Scintillation detector 3400 is, for example, one of scintillation detectors 700, 800, 900, 1070, 1170, 2800, 2900, 3000, 3100, and 3270. Scintillation detector 3400 includes a scintillator substrate 715 and plurality of photodetectors 710(1-N) each in optical communication with one of a respective plurality of edge region locations 3412(1-N) on one of edge surfaces 706 of scintillator substrate 715. Edge region locations 3412 are stored in memory 3460 of data processor 3402 and may be distinct and non-overlapping.

Memory 3460 may be transitory and/or non-transitory and may include one or both of volatile memory (e.g., SRAM, DRAM, or any combination thereof) and nonvolatile memory (e.g., FLASH, ROM, magnetic media, optical media, or any combination thereof). Part or all of memory 3460 may be integrated into microprocessor 3432.

Memory 3460 also stores detector parameters 3405 associated with scintillation detector 3400. Examples of detector parameters 3405 include the detectors MDRF (e.g. MDRFs 1500, 1700, 1900, and 2500) and in some embodiments grid-point images (e.g., grid-point images 1600 and 2600) and resolution maps derived from a grid-point image. Detector parameters 3405 may also include detector geometry, such as spatial dimensions of scintillator substrate 715 and detectors 710. Software 3420 includes an estimator 3422, which may include at least one of the following estimation methods: maximum likelihood, contracting-grid maximum likelihood search, least-squares, iterative, LN norm comparisons (where N is 0, 1, 2 . . . ), and an Anger method. In an embodiment, an energy window or timing coincidence window is applied before the estimation of the gamma-ray interaction position. These window limits are also stored in memory 3460. In an embodiment, a likelihood threshold (lower bound, if using Maximum likelihood estimation), LN norm threshold (upper bound, if using LN norm comparison) are also stored inside the memory 3460.

In a use scenario, a scintillation event 3401 occurs in substrate 715, as illustrated in FIG. 34. When PET scanner 3490 detects scintillation event 3401, detectors 710(1-N) of scintillation detector 3400 generate respective electrical signal amplitudes 3400D(1-N) which data processor 3402 receives and stores in memory 3460. Estimator 3422 generates lateral coordinates 3491 of the scintillation event from detector parameters 3405, edge region locations 3412, and electrical signal amplitudes 3400D.

Figure 35:
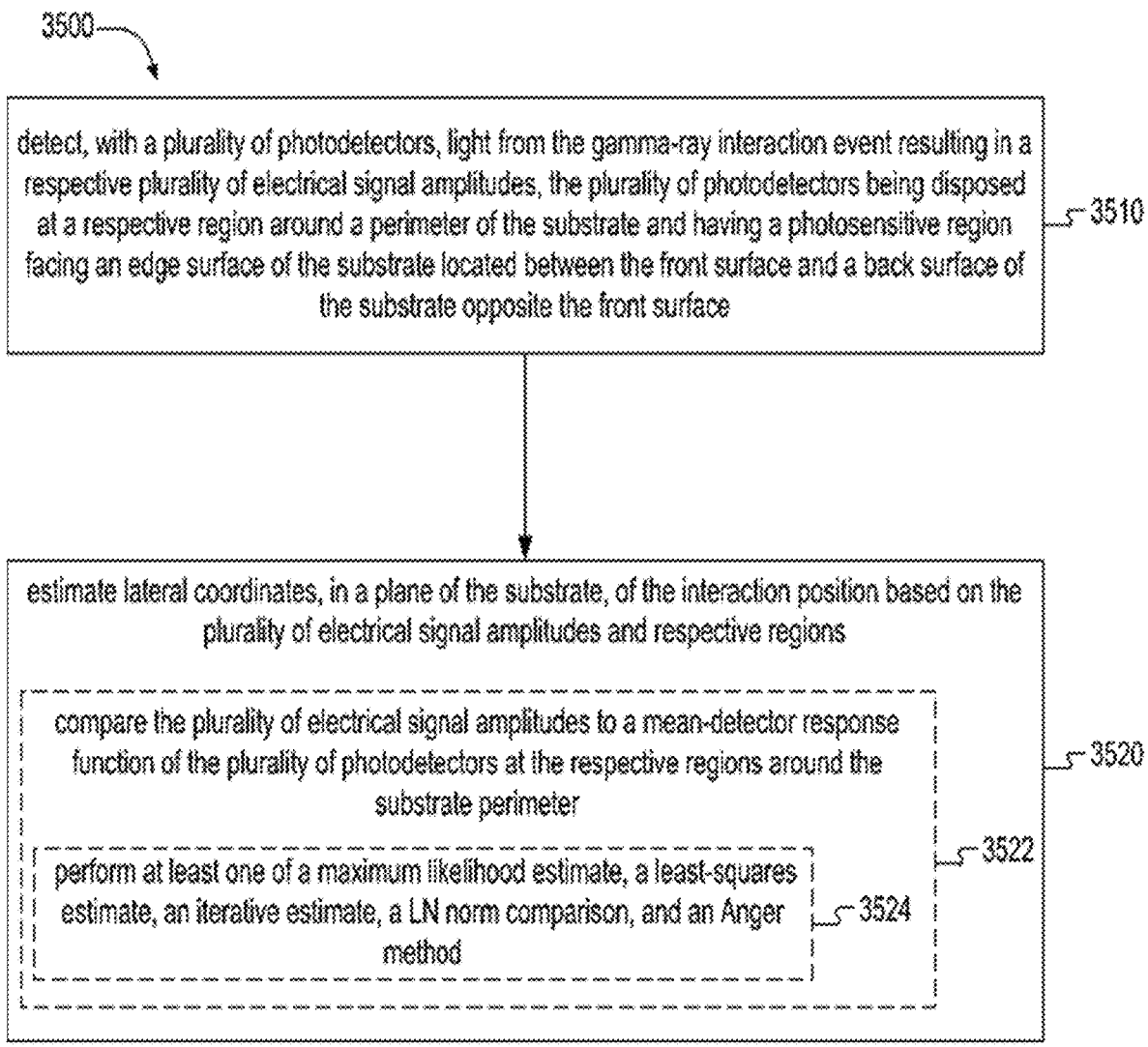
FIG. 35 is a flowchart illustrating an embodiment of a method for determining interaction position of a gamma-ray interaction event.

FIG. 35 is a flowchart illustrating a method 3500 for determining the interaction position of a gamma-ray interaction event, occurring in a substrate resulting from electromagnetic radiation incident on a front surface of the substrate. Method 3500 includes at least one of steps 3510, 3520, 3522, and 3524. Method 3500 is, for example, implemented by microprocessor 3432 executing computer-readable instructions of software 3420.

Step 3510 comprises detecting, with a plurality of photodetectors, light from the gamma-ray interaction event resulting in a respective plurality of electrical signal amplitudes. Each of the plurality of photodetectors having a respective photosensitive region in optical communication with one of a respective plurality of regions of an edge surface of the substrate located between a front perimeter of the front surface and a back perimeter of a back surface of the substrate opposite the front surface. In an example of step 3510, scintillation detector 3400 detects light from scintillation event 3401 having occurred within scintillator detector 3400.

Step 3520 comprises estimating lateral coordinates, in a plane of the substrate, of the interaction position based on the plurality of electrical signal amplitudes and respective regions. In an example of step 3520, estimator 3422 generates lateral coordinates 3491 from electrical signal amplitudes 3400D.

Step 3520 may include step 3522 of comparing the plurality of electrical signal amplitudes to a mean-detector response function of the plurality of photodetectors at the respective regions around the substrate perimeter. In an example of step 3520, estimator 3422 generates lateral coordinates 3491 from mean detector parameters 3405, electrical signal amplitudes 3400D, and optionally edge region locations 3412.

Step 3522 may include step 3524 of performing at least one of a maximum likelihood estimate, a least-squares estimate, an iterative estimate, LN norm comparison (where N can be 0, 1, 2, 3, 4, 5 . . . , and a combination of L1 with L2, L2 with L4, etc.), and an Anger method. In an example of step 3522, estimator 3422 uses at least one of a maximum likelihood estimate, a least-squares estimate, an iterative estimate, and an Anger method to generate lateral coordinates 3491 from detector parameters 3405, edge region locations 3412, and electrical signal amplitudes 3400D.

Example 2

Simulation of a CsI/LYSO Detector Layer. This section describes simulation of crystals that that were tested experimentally. The geometry of the scintillation crystal was set as 27.4 mm×27.4 mm×3 mm. Sixteen SiPMs were attached to the edges of the scintillation crystal with 4 SiPMs on each edge. Several factors influencing the spatial resolution were studied:
  gamma-ray photon energy and scintillator material (662 keV for CsI(Tl) vs 511 keV for LYSO);
  optical barriers (with/without);
  optical-gel & SiPM-window refractive indices (1.5 vs 1.82).

The dark-count rate was set to 2 MHz/SiPM in accordance with the Hamamatsu S13360-6050PE MPPC data sheet. The readout shaping time was set to 4 µs for CsI(Tl) and 150 ns for LYSO, based on their published decay times (Mao R, Zhang L, Zhu, R. Optical and Scintillation Properties of Inorganic Scintillators in High Energy Physics. *IEEE Transactions on Nuclear Science*. 2008; 55(4): 2425-2431). The optical-gel/SiPM-window materials' refractive indices were studied to evaluate the effect of reflectance at the edge boundaries. The simulated resolutions (evaluated at 20×20 positions by a narrow beam of gamma-ray photons) are shown in Table I.

TABLE I

Factors that influence spatial resolution based on simulated data.

| Spatial Resolution Factors | | | Edge-coupling index 1.5 | Edge-coupling index 1.82 |
|---|---|---|---|---|
| without optical barrier | CsI(Tl) @ 662 keV | Whole | 0.69 ± 0.31 mm | 0.53 ± 0.16 mm |
| | | Center | 0.55 ± 0.08 mm | 0.75 ± 0.08 mm |
| | LYSO @ 511 keV | Whole | 0.98 ± 0.43 mm | 0.75 ± 0.23 mm |
| | | Center | 0.78 ± 0.11 mm | 1.06 ± 0.11 mm |
| with optical barrier | CsI(Tl) @ 662 keV | Whole | 0.38 ± 0.20 mm | 0.23 ± 0.07 mm |
| | | Center | 0.22 ± 0.08 mm | 0.22 ± 0.09 mm |
| | LYSO @ 511 keV | Whole | 0.57 ± 0.31 mm | 0.33 ± 0.09 mm |
| | | center | 0.34 ± 0.12 mm | 0.32 ± 0.13 mm |

Figure 36:
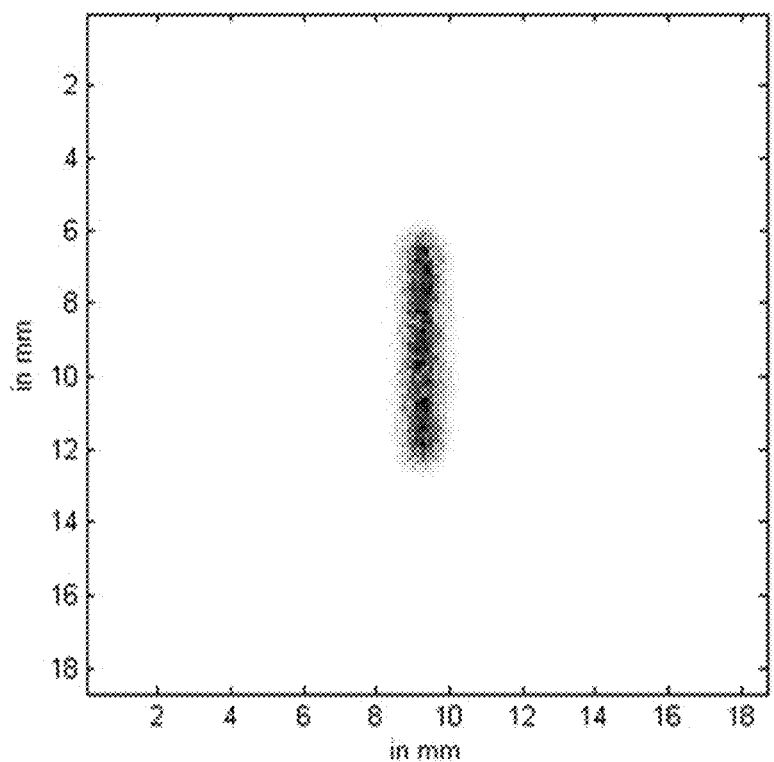
FIG. 36 is a simulated projection image formed with a slit having a width corresponding to a width of a gamma-ray photon beam used to illuminate an embodiment of a scintillation detector without optical scatterers.
Figure 37:
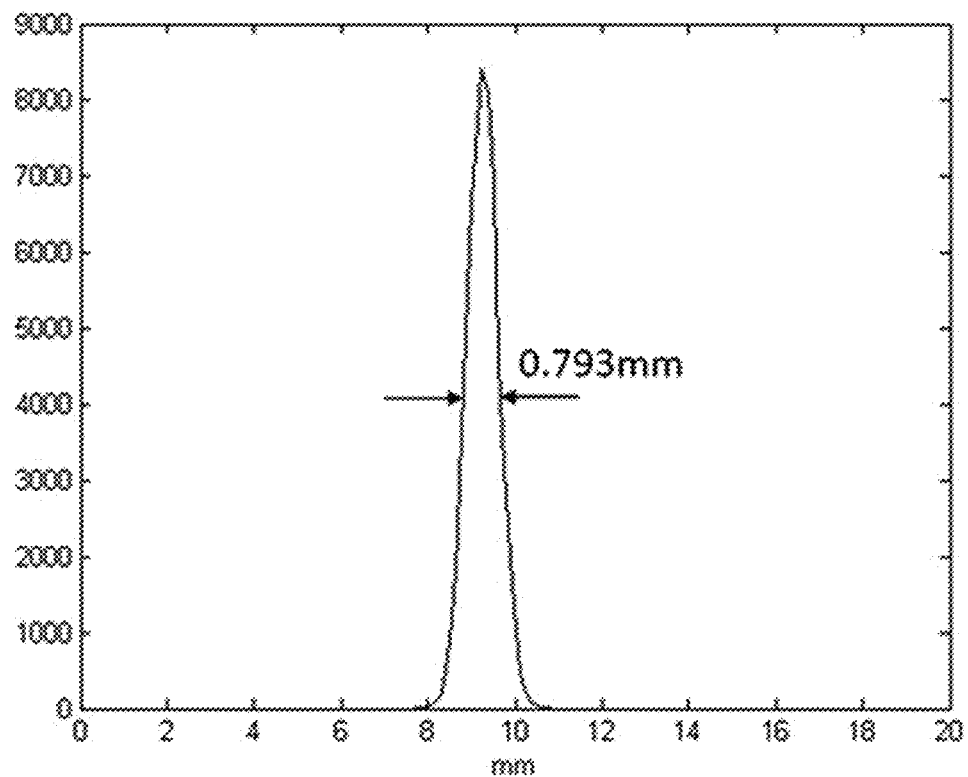
FIG. 37 is a plot illustrating spatial profile of the projection image of FIG. 36.
Figure 38:
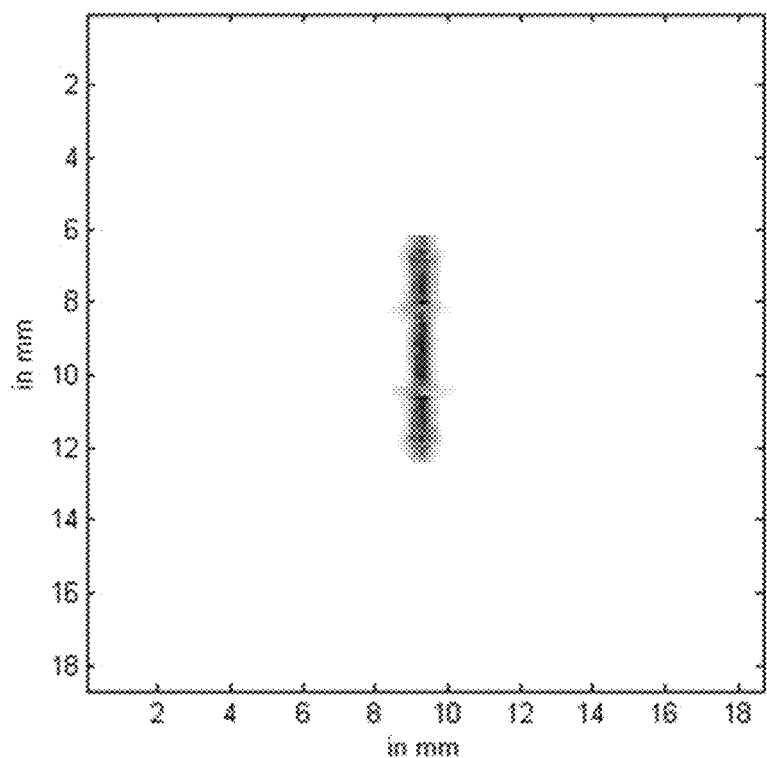
FIG. 38 is a simulated projection image formed with a slit having a width corresponding to a width of a gamma-ray photon beam used to illuminate an embodiment of a scintillation detector with drilled-hole-type of optical scatterers.
Figure 39:
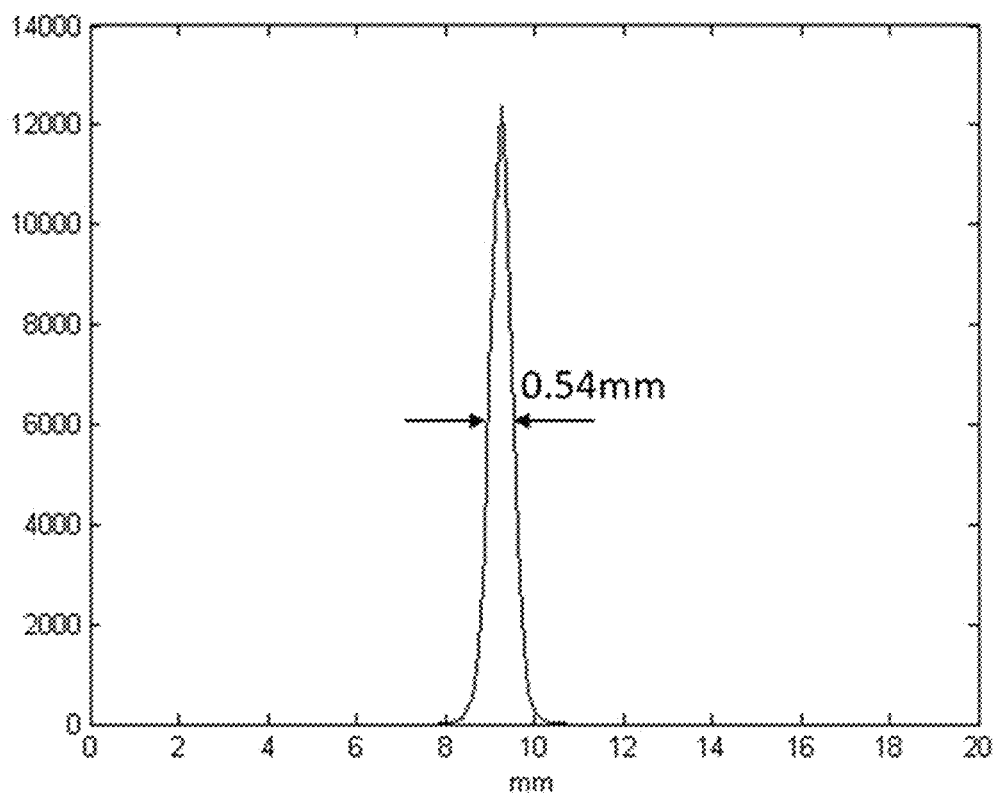
FIG. 39 is a plot illustrating spatial profile of the projected image of FIG. 38.

*Whole: average spatial resolution of the whole detector region (27.4 mm × 27.4 mm)
*Center: average spatial resolution of the center region (15 mm × 15 mm)
* Edge-coupling index: the refractive index of the optical-gel and SiPM-window material A slit beam of 662-keV gamma photons was also simulated to verify the experiment described below. The width of the simulated beam was 0.44 mm (FWHM of a Gaussian profile). The resulting projection images for detectors without and with optical barriers are shown in FIGS. 36-37 and 38-39, respectively. FIG. 36 is a simulated projection image by a slit of width 0.44 mm. FIG. 37 is a profile of the projection image of FIG. 36. with indicated FWHM, on the prototype detector (27.4 mm×27.4 mm×3 mm CsI(Tl), with sixteen SiPMs) without optical barriers. FIG. 38 is a simulated projection image by a slit of width 0.44 mm. FIG. 39 is a profile of the projected image of FIG. 38 with indicated FWHM, on the prototype detector with drilled-hole optical barriers.

Experimental Verification

Figure 40:
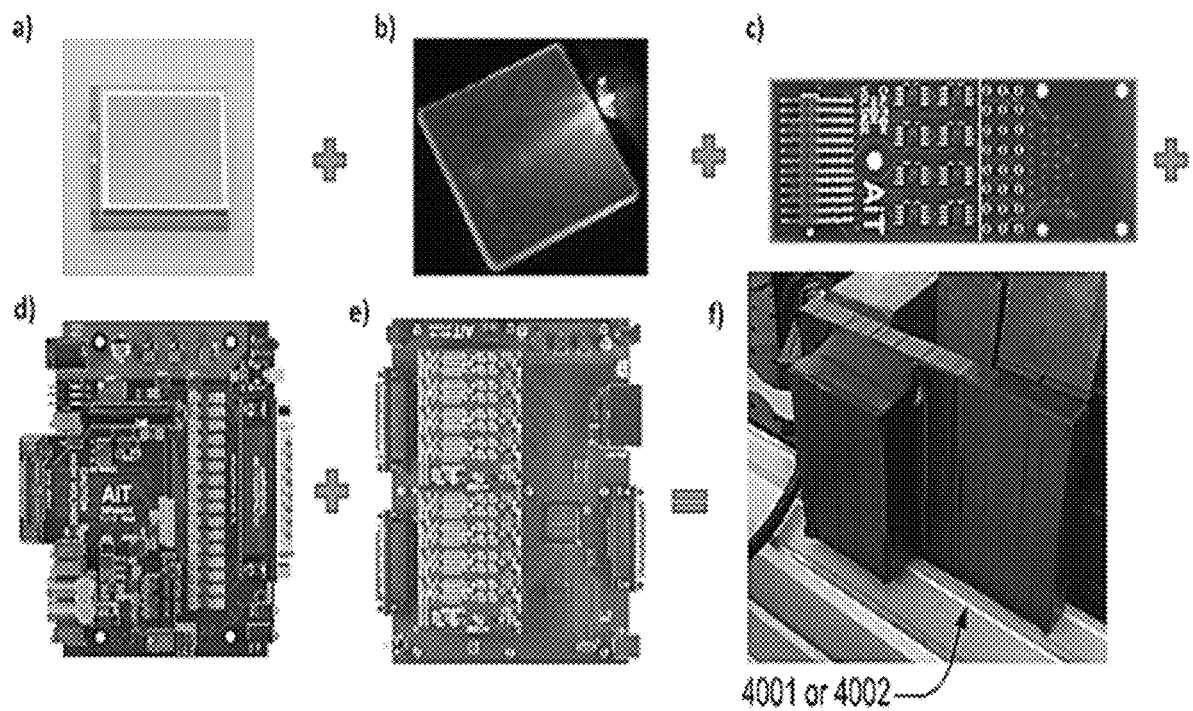
FIG. 40 (panels a, b, c, d, e, and f) includes photographs of components of a an embodiment of a prototype detector.

FIG. 40 includes photographs of components of a prototype detector 4001 and 4002. The prototype detector includes the following components, labelled (a) through (e) in FIG. 40:

(a) Sixteen Hamamatsu S13360-6050PE MPPCs (SiPMs);
(b) CsI(Tl) scintillation crystal: CsI(Tl) crystal of dimension 27.4 mm×27.4 mm×3 mm (obtained from *Proteus*, without mechanical holes as in detector 4001, and with mechanical holes, as in detector 4002);
(c) pre-amplifier circuit;
(d) amplifier and analog-to-digital-converting circuit;
(e) FPGA data acquisition circuit (AiT 16-channel-read-out circuit).

The photograph labelled (f) is prototype detector 4001 or 4002.

The scintillator was chosen to be CsI(Tl) for convenience (no background activity from the crystal and low hygroscopicity). The MDRFs were acquired by scanning the detector with a crossed-slit-collimated beam of 662 keV photons from a $^{137}$Cs source. The beam size on the detector surface was measured to be about 0.44 mm×0.44 mm (FWHM) with an intensified quantum imaging detector (iQID) camera (Miller B W, Gregory S J, Fuller E S, Barrett Barber H B, Furenlid L R. The iQID camera: An ionizing-radiation quantum imaging. *Nucl Instrum Methods Phys Res A*. 2014; 11(767): 146-152). Due to a limited dynamic range in the AiT readout electronics, only the center area of the detector was calibrated (15.0 mm×15.0 mm) and used for imaging.

Experiment Case 1: Without Optical Barrier

Figure 41:
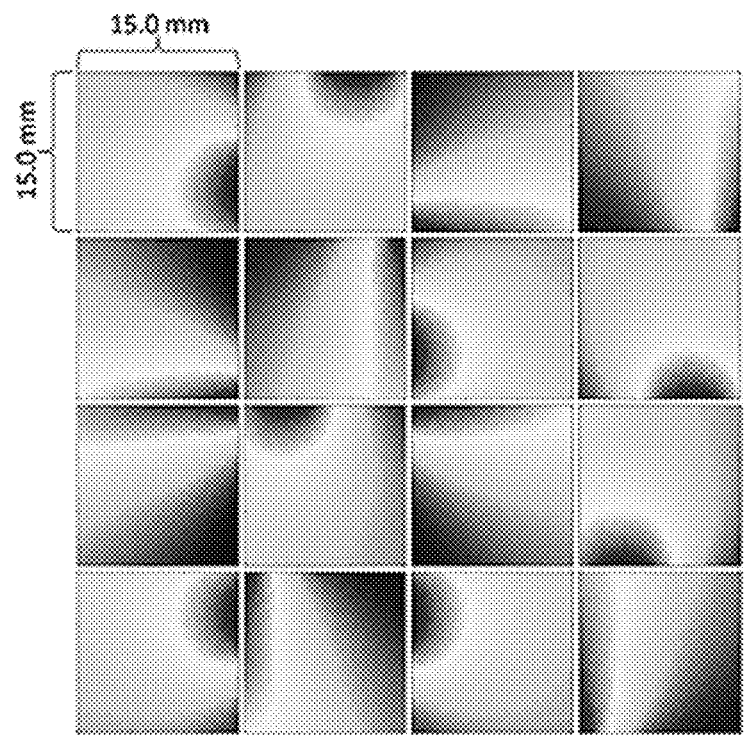
FIG. 41 illustrates measured MDRF of the prototype detector of FIG. 40 (when such detector does not contain/lacks optical scatterers.
Figure 42:
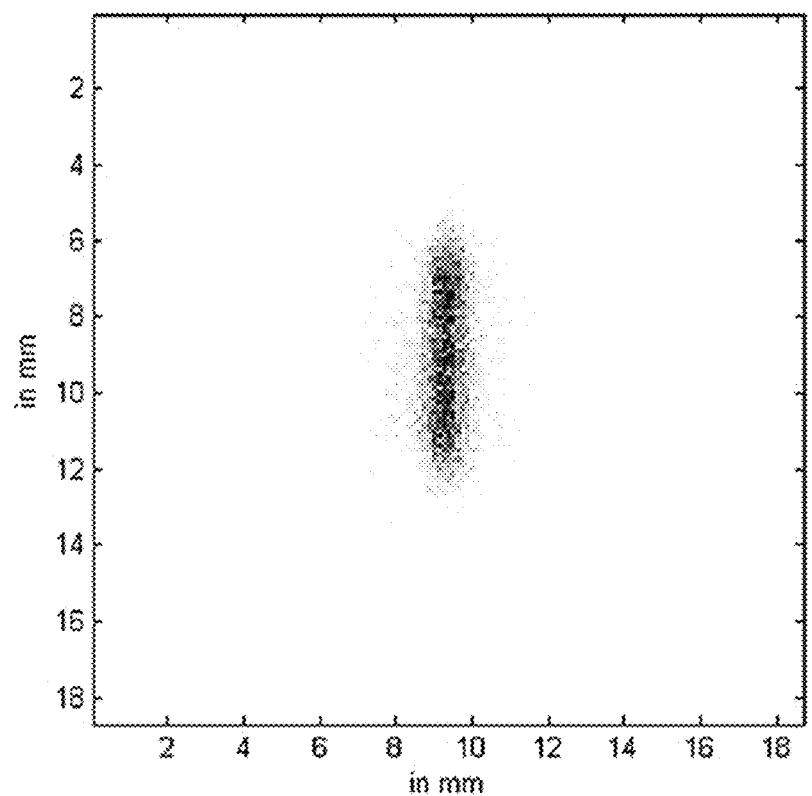
FIG. 42 is a measured projection image of a slit having a width equal to that of a gamma-ray photon beam used to evaluate positioning performance of the prototype detector of FIG. 40 (when such detector lacks optical scatterers).
Figure 43:
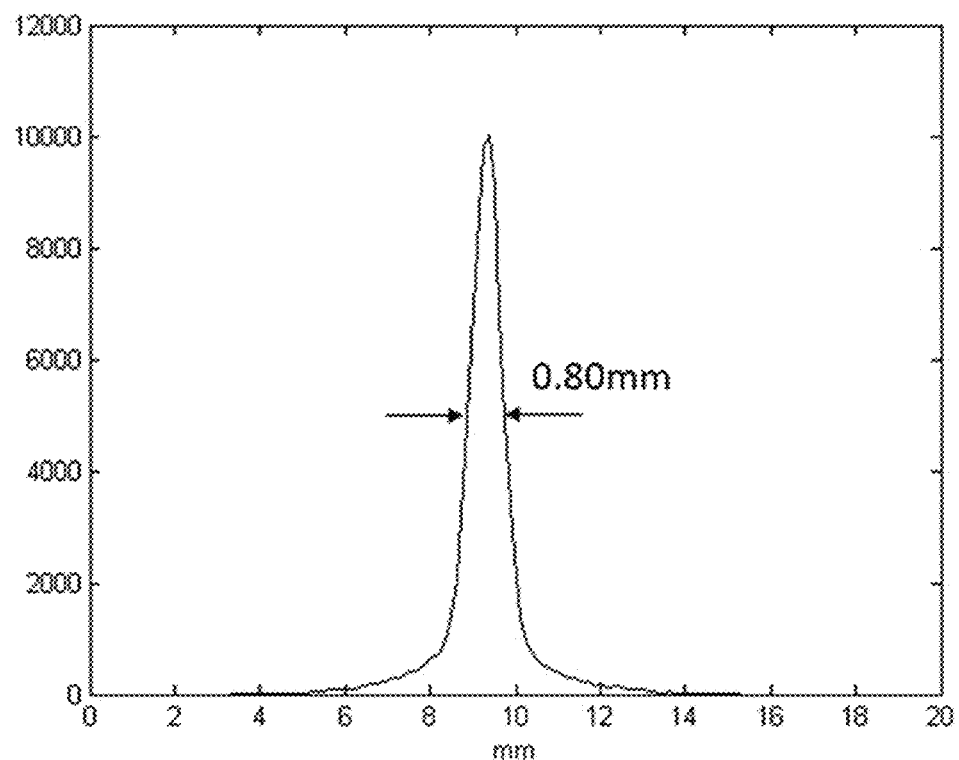
FIG. 43 is a spatial profile of the projection image of FIG. 42.

The measured MDRFs of the CsI(Tl) crystal without optical barriers present are shown in FIG. 41. FIG. 41 illustrates measured MDRF of prototype detector 4001 without optical barriers, created by scanning a thin beam of 662-keV gamma-ray photons (0.44 mm×0.44 mm, FWHM), in a regular array of positions across the detector A slit projection of 662-keV photons of width 0.44 mm (FWHM of a Gaussian profile, as measured with the iQID camera) was used to evaluate the positioning performance. The resulting projection image and cross-sectional profile are shown in FIGS. 42 and 43, respectively. FIG. 42 is a measured projection image by a slit of width 0.44 mm. FIG. 43 is a profile of the projection image of FIG. 42 with indicated FWHM, on the prototype detector (27.4 mm×27.4 mm×3 mm CsI(Tl), with sixteen SiPMs) without optical barriers.

Experiment Case 2: With Optical Barrier

Figure 44:
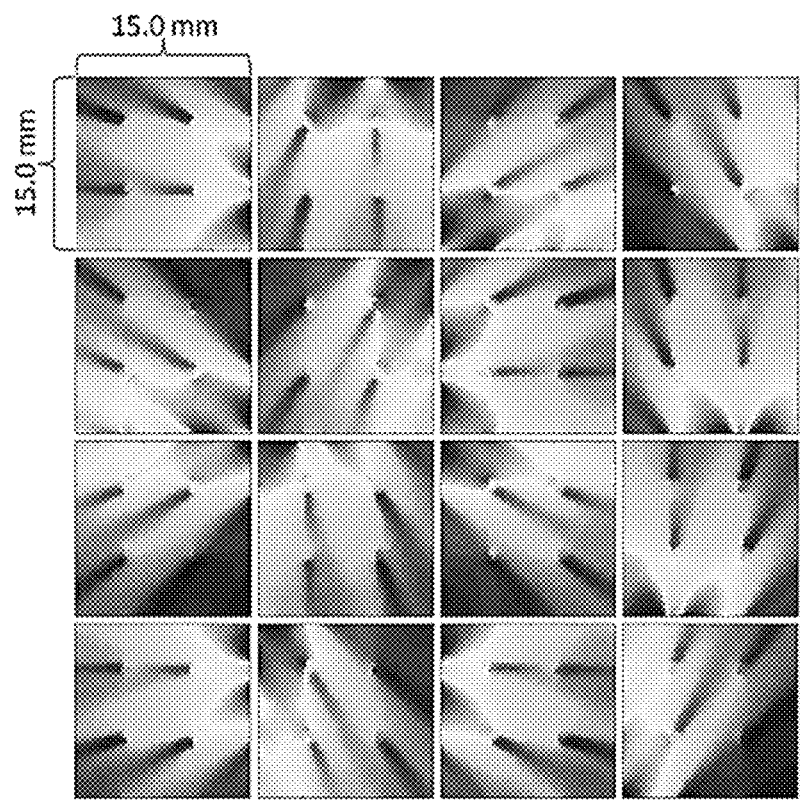
FIG. 44 illustrates measured MDRF of a prototype detector of FIG. 40 (when such detector includes drilled-hole optical barriers in the scintillation crystal).

With optical barriers, created by mechanically-drilled holes (with Teflon lining the holes) in a substrate of a scintillation detector, the resolution can be greatly improved. FIG. 44 illustrates measured MDRF of prototype detector 4002, when the scintillation crystal includes drilled-hole optical barriers. The MDRF was created by scanning a thin beam of 662-keV gamma photons across the central area of the detector.

Figure 45:
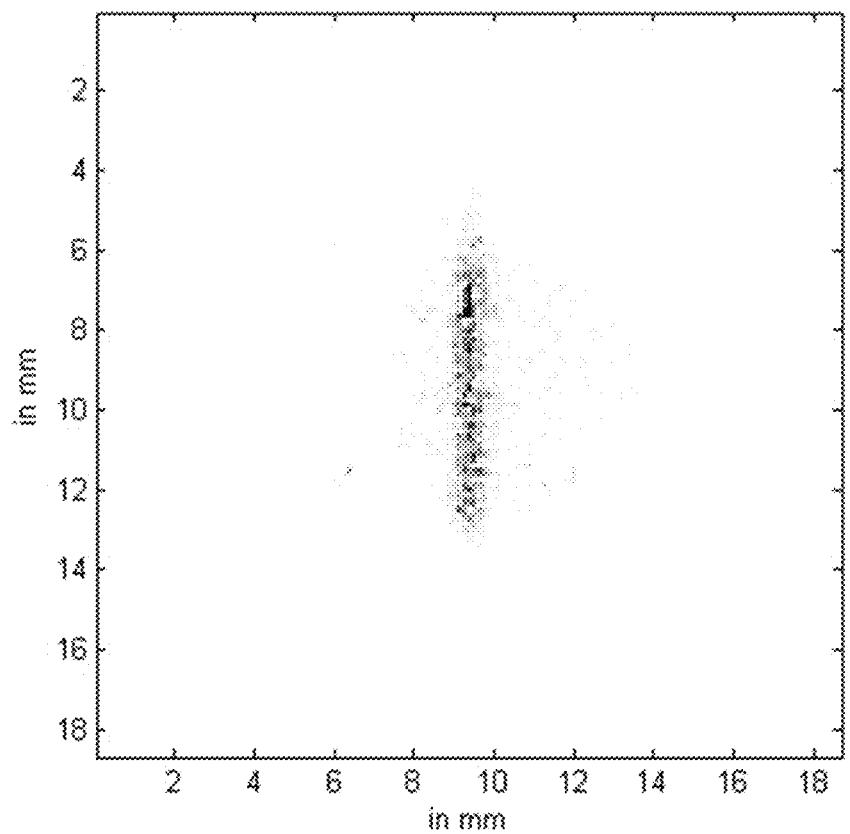
FIG. 45 is a measured projection image of a slit having a width equal to that of a gamma-ray photon beam used to evaluate positioning performance of the prototype detector of FIG. 40 (when such detector includes optical barriers).
Figure 46:
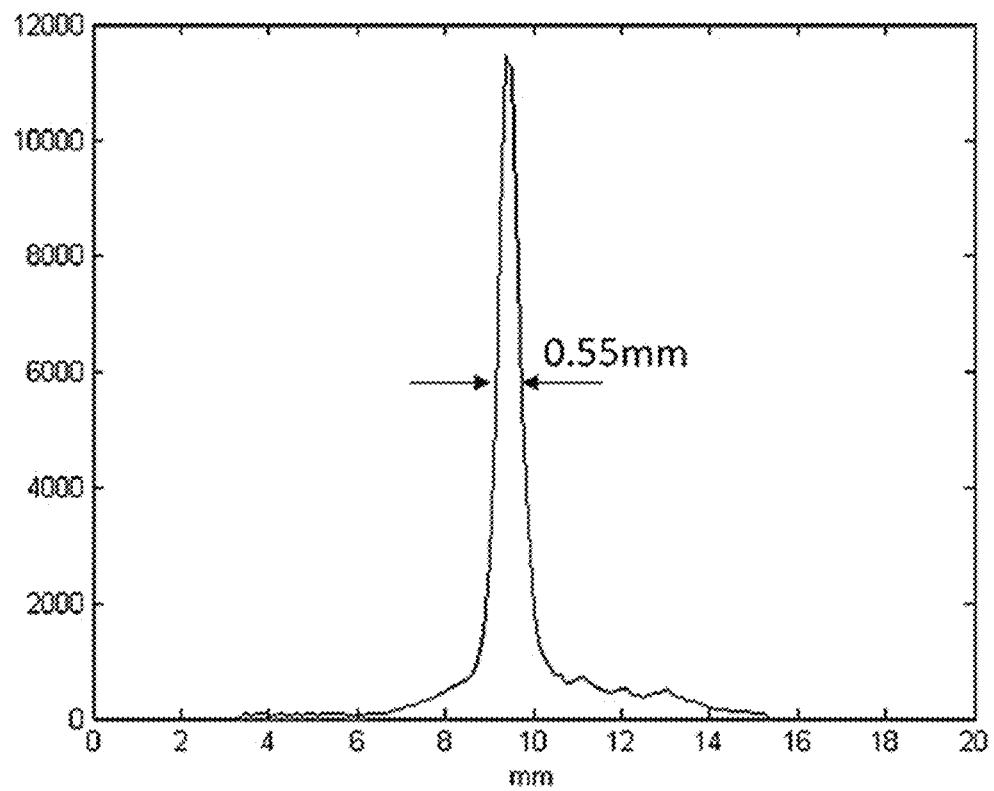
FIG. 46 is a spatial profile of the projection image of FIG. 44.
Figure 47:
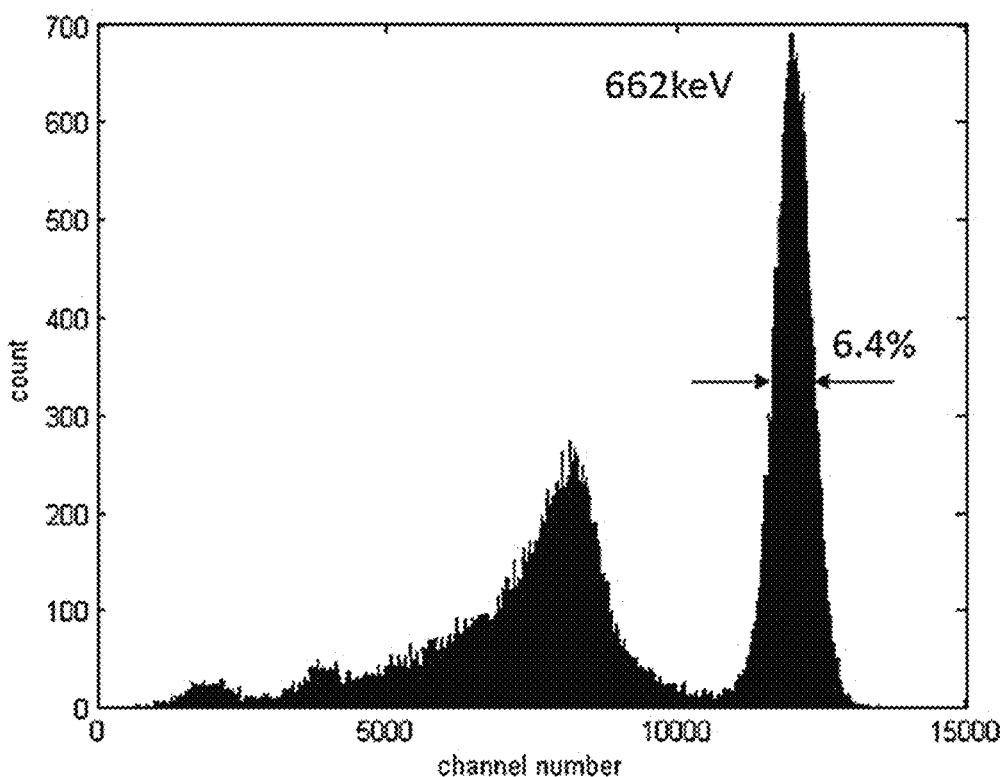
FIG. 47 is a position-corrected (method described below) energy spectrum of a flood image by $^{137}$Cs, using crystal CsI(Tl).

Again, the performance was evaluated by a slit beam of 662-keV photons of width 0.44 mm (FWHM). The resulting projection image and cross-sectional profile is shown in FIGS. 45 and 46, respectively. A position-corrected (method described below) energy spectrum of a flood image by $^{137}$Cs is shown in FIG. 47.

The Monte-Carlo simulation indicates that the PET-block-detector-sized design (50.8 mm×50.8 mm×3 mm LYSO crystal) can provide reasonable spatial resolution even without optical barriers (the average FWHM is 1.49 mm), and excellent spatial resolution with drilled-hole optical barriers (the average FWHM is 0.56 mm) or laser-etched pattern optical barriers (the average FWHM is 0.62 mm). It is worth mentioning that the introduction of mechanically drilled-hole optical barriers will decrease the sensitivity a little bit, which is less than 2% in this simulation, while the majority of the detection efficiency loss is due to the gaps between different detector modules, since the SiPMs and associated readout circuitry will occupy the gaps. For example, for a crystal area of 50.8 mm×50.8 mm with 3 mm gap between the detector modules, the sensitivity reduction is about 11%. So, the key to minimize the sensitivity loss is to minimize the gaps between detector modules.

A further Monte-Carlo simulation suggests that the optical-gel/SiPM-window materials' refractive indices have a great impact on the detector's spatial resolution. Whether a photon has a chance to be reflected at the detector edge interface by undesired TIR is determined by the minimum refractive index on its path from the scintillation crystal to the silicon substrate of the SiPM. As TABLE I shows, if the minimum refractive index on its path is 1.5, the overall spatial resolution will degrade by a few hundred microns. However, the central area spatial resolution may actually be improved due to the relatively steeper gradient features in the MDRFs in the center area, created by TIR at the edges.

Figure 48:
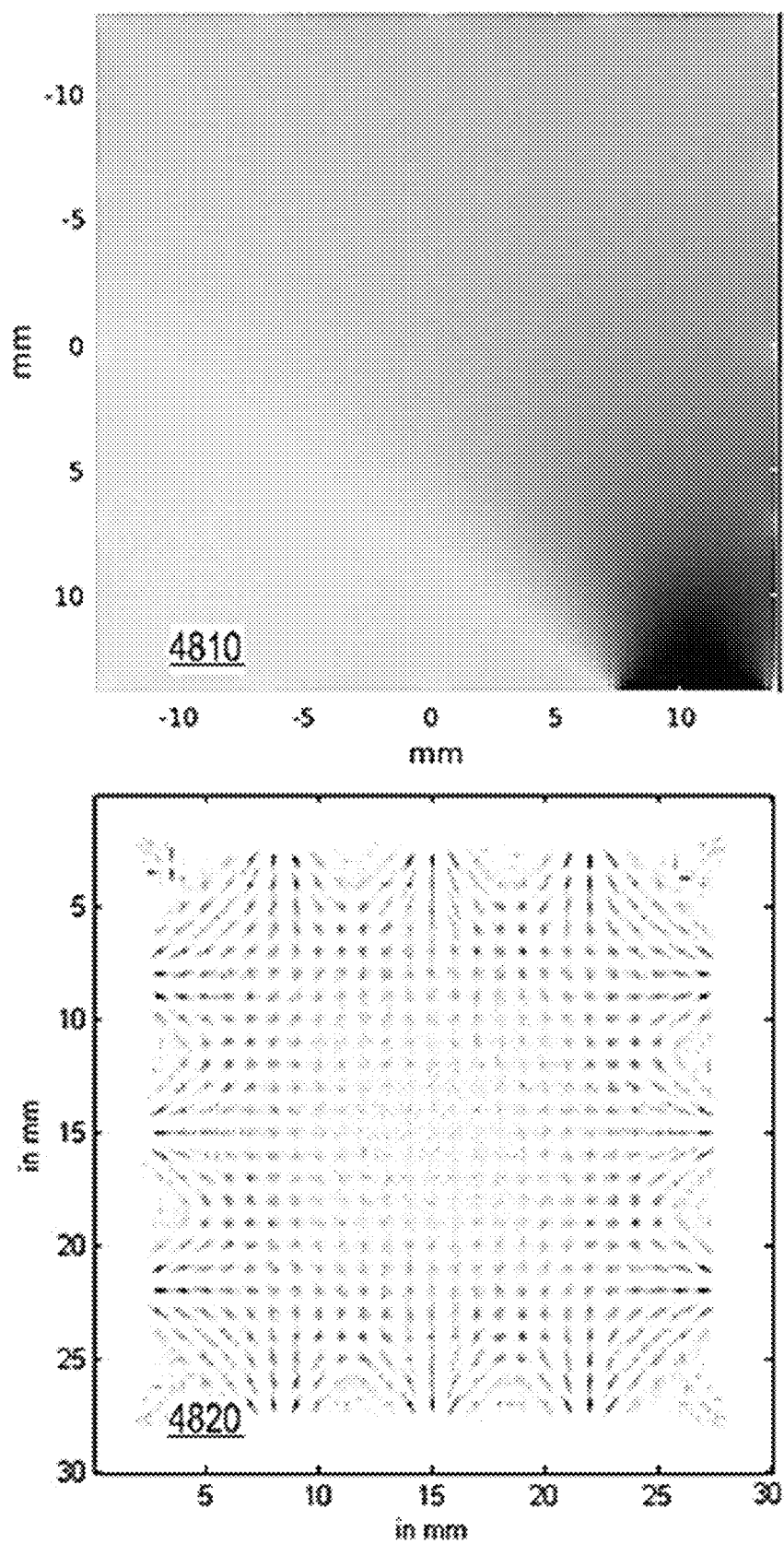
FIG. 48 illustrates an MDRF for refractive index of edge optical-gel/SiPM-window set to 1.5 (in an upper panel of FIG. 48) and a corresponding point-grid image (in the lower panel of FIG. 48).
Figure 49:
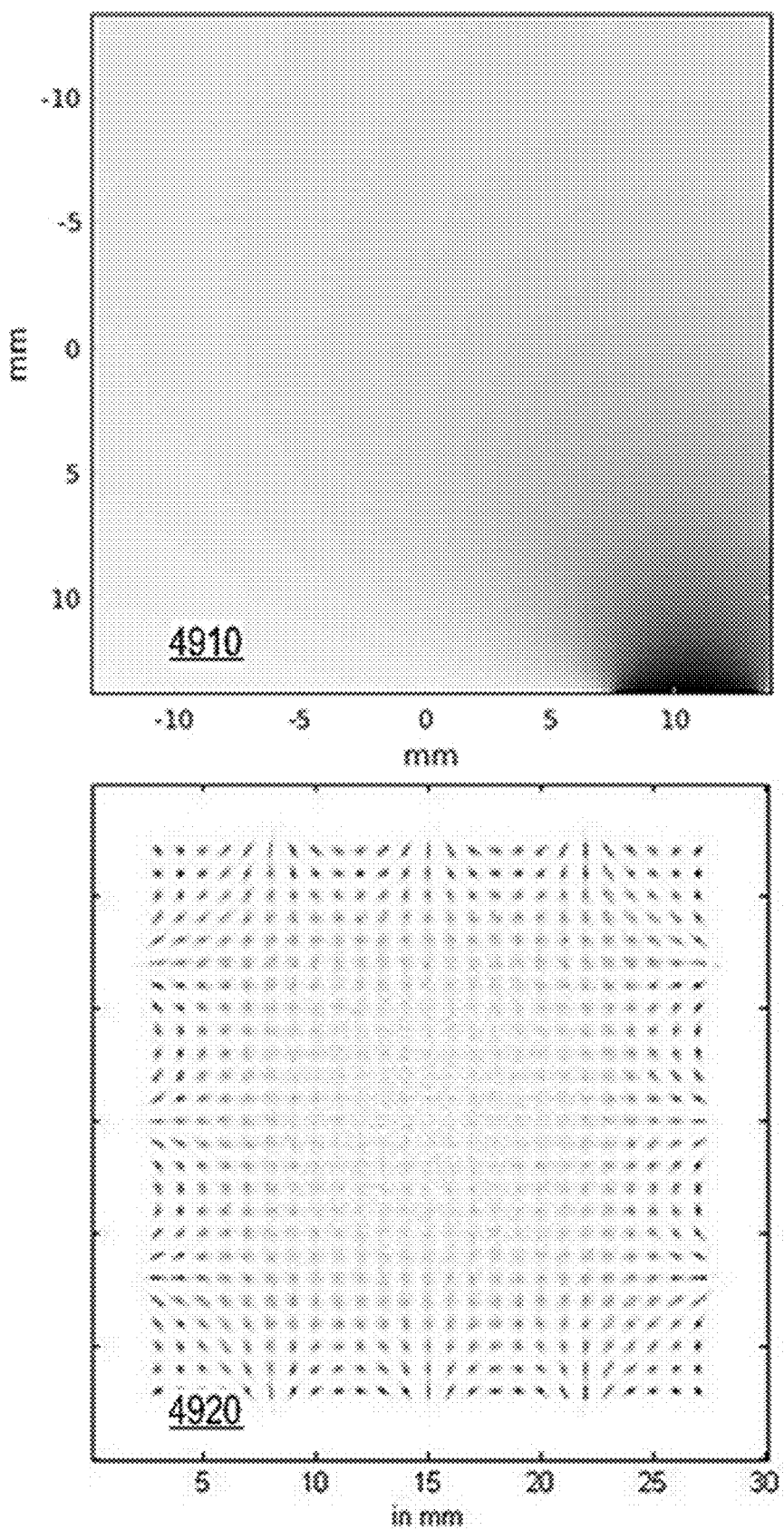
FIG. 49 illustrates an MDRF for refractive index of edge optical-gel/SiPM-window set to 1.82 (in an upper panel of FIG. 49) and a corresponding point-grid image (in the lower panel of FIG. 49).
Figure 50:
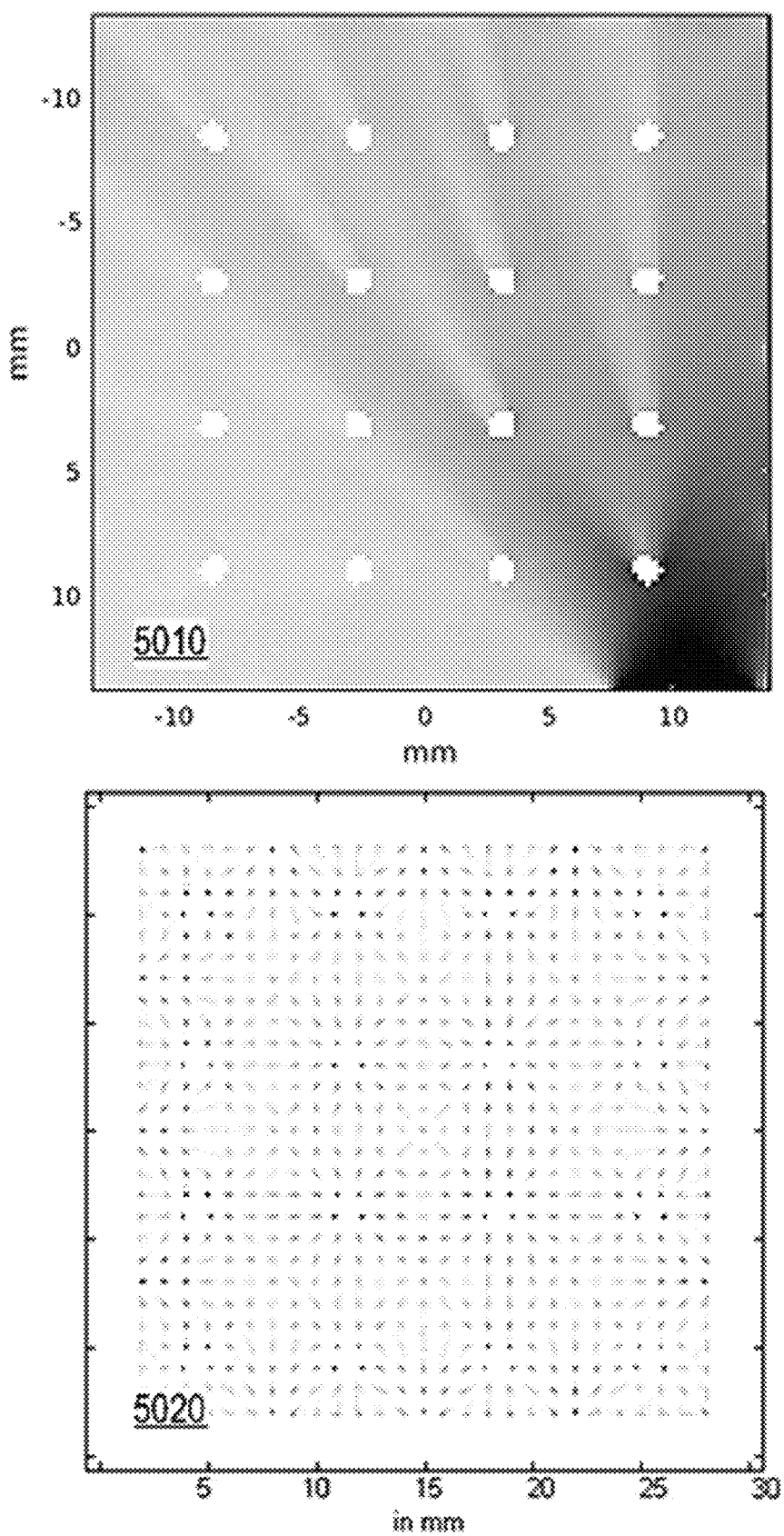
FIG. 50 illustrates an MDRF for refractive index of edge optical-gel/SiPM-window set to 1.5, but with optical barriers in the scintillation crystal (in an upper panel of FIG. 50), and a corresponding point-grid image (in the lower panel of FIG. 50).

To understand this effect, the detector's (without optical barriers) simulated central-region MDRFs for minimum refractive indices of 1.5 and 1.82 were compared, as shown in FIGS. 48-50. FIG. 48 illustrates an MDRF 4810 for refractive index of edge optical-gel/SiPM-window set to 1.5 and a corresponding point-grid image 4820. FIG. 49 illustrates an MDRF 4910 for refractive index of edge optical-gel/SiPM-window set to 1.82 and a corresponding point-grid image 4920. FIG. 50 illustrates an MDRF 5010 for refractive index of edge optical-gel/SiPM-window set to 1.5, but with optical barriers in the scintillation crystal, and a corresponding point-grid image 5020.

If the optical-gel/SiPM-window material had the lower index of 1.5 and a line connecting the gamma-ray interaction position and the center of the SiPM exceeded the TIR critical angle, then a steep drop in the MDRF value was observed. The spatial resolution will then be worse at proximities close to each SiPM and corner regions of the crystal. If the optical-gel/SiPM-window material had the larger refractive index of 1.82, there was no TIR, and all of the MDRFs' position dependence was due to the solid angle subtended by the area of the SiPM relative to origin of scintillation photons at the gamma-ray interaction location. If optical barriers are added, which are close to crystal boundaries, then the spatial resolution close to the crystal boundaries can be improved. Overall, high reflectance at the crystal-to-SiPM coupling layer can decrease the spatial resolution near crystal edges, but optical barriers can help to offset this effect, as shown in FIGS. 48-50.

The experimental results demonstrated the potential of this detector design. The spatial resolution for the crystal without optical barriers was calculated based on the slit projection image. By summing along the vertical direction of FIG. 42, the resulting profile plot is shown in FIG. 43. The FWHM was measured to be 0.80 mm. Assuming the line-spread function of the slit approximates a Gaussian profile, the spatial resolution (FWHM) is estimated to be: $\delta=(0.80^2-0.44^2)^{0.5}=0.67$ mm. For comparison, the simulated slit image of the prototype detector without optical barriers (FIGS. 35-36) yielded a spatial resolution of: $\delta_{simulation} \approx 0.65$ mm. The experimental result was quite close to that predicted by simulation.

The procedure was repeated for the detector with optical barriers. The spatial resolution of the prototype detector with optical barriers was measured to be: $\delta_{experiment} \approx 0.34$ mm, while the simulated resolution was predicted to be: $\delta_{simulation} \approx 0.31$ mm. The measured spatial resolution is a little worse than that predicted by simulation, which is expected, since the simulation does not include all electronic noise sources.

The energy resolution of the prototype detector with optical barriers was measured by exposing the detector to the $^{137}$Cs source without collimation. First a flood image was acquired, and each event's position in the flood image was estimated using the measured MDRF. Each event's summed-SiPM-signal value was also binned according to its estimated position. Then, the average energy at each position was calculated and stored in a 61×61 matrix (0.25 mm step size). This matrix was used for position-dependent energy correction. A second flood image was acquired that generated the energy spectrum including position-dependent correction (FIG. 47). The FWHM energy resolution ($\Delta E/E$) was estimated to be 6.4% at 662 keV, which is very good for a CsI(Tl) detector (see Kazuch et al. Non-Proportionality and Energy Resolution of CsI(Tl). *IEEE Transactions on Nuclear Science*. 2007; 54(5): 1836-1841; and Becker et al., Small Prototype Gamma Spectrometer Using CsI(Tl) Scintillator Coupled to a Solid-State Photomultiplier. *IEEE Transactions on Nuclear Science*. 2013; 60(2): 968-972)).

Discussion

The edge readout detector design described in the above examples can easily reach <1 mm resolution with the help of optical barriers, while simultaneously achieving good gamma-ray detection efficiency via multiple layers, thus avoiding the usual tradeoff between spatial resolution and gamma-ray detection sensitivity. The energy resolution of this design is also excellent due to the large fraction of photons arriving at crystal edges. Also, due to the monolithic design, there are no pixel gaps with reflective material, which further increases the gamma-ray detection sensitivity. The direct DOI estimation gives this design even more advantages over traditional PET detectors, and multi-position energy-deposition events across different layers caused by Compton scatter can, in principle, be identified. The first interaction position can often be estimated, from Compton kinematics which can help improve the spatial resolution. The effort of scintillator cutting and surface treatment is reduced due to the non-pixelated design. The detector design is also capable of working as a high-sensitivity Compton camera for high-energy gamma-ray photons when outfitted with fast timing electronics. Additionally, multiple modules can be tiled to produce cameras for SPECT.

In addition to the above, additional features or operating conditions may be utilized to improve detector performance. For instance, a large number of readout channels may be present when multiple layers are combined. FIG. 11 shows a 6-layer design in which there may be a total of 120 readout channels for a complete detector module. Accordingly, if necessary, the number of readouts can be reduced or compact FPGA-based readout circuits may be utilized to handle large numbers of light sensors. When optical barriers are used, the MDRFs contain many sharp features that can create local likelihood-maxima. Thus, algorithms can be further utilized to carry out the positon estimation of each event quickly and accurately. In addition, since multiple SiPMs' signals are added to produce a pulse for time stamp, the noise in different channels will also be added together, thus potentially affecting the coincidence timing resolution. The noise from dark count and circuit can be suppressed or reduced by cooling if necessary. The gaps between detector modules should also be minimized to preserve the detection efficiency. This can be achieved by making SiPMs and the pre-amplifiers thinner.

The edge-readout detector design described in the above experiments exhibits many appealing features. These include excellent spatial resolution, good energy resolution, and the ability to recover DOI information. The reduced fabrication effort is further appealing for clinical applications, including but not limited to human brain PET.

Combinations of Features.

Features described above as well as those claimed below may be combined in various ways without departing from the scope hereof. The following examples illustrate some possible, non-limiting combinations:

(A1) A scintillation detector comprising a scintillator substrate and a plurality of photodetectors. The scintillator substrate comprises an interior bound by a front surface having a front perimeter, a back surface opposite the front surface and having a back perimeter, and an edge surface between the front and back perimeters. Each of the plurality of photodetectors has a respective photosensitive region facing or otherwise in optical communication with one of a respective plurality of regions of the edge surface.

(A2) In the scintillation detector denoted by (A1), the front surface may be a planar surface, and the back surface being a planar surface substantially parallel to the front surface.

(A3) In any scintillation detector denoted by one of (A1) and (A2), the scintillator substrate may have a uniform thickness between 0.5 millimeters and twenty millimeters, optionally between one millimeter and four millimeters.

(A4) In any scintillation detector denoted by one of (A1) through (A3), the front perimeter may have a front shape that is geometrically similar to a back shape of the back perimeter, the front shape being a polygon.

(A5) In any scintillation detector denoted by one of (A1) through (A4), the scintillation detector may have one of a rectangular, hexagonal, and octagonal shape.

(A6) In any scintillation detector denoted by one of (A1) through (A5), the substrate may include a scintillator material and may have a refractive index exceeding 1.1 at an emission maximum of the scintillator material.

(A7) In any scintillation detector denoted by one of (A1) through (A6), each of the plurality of photodetectors may be attached to the scintillator substrate (A8) In any scintillation detector denoted by one of (A1) through (A7), each of the plurality of photodetectors may include a silicon photomultiplier, photomultiplier tube, avalanche photodiode, complementary metal-oxide semiconductor, or a combination thereof.

(A9) In any scintillation detector denoted by one of (A1) through (A8), each of the plurality of photodetectors may include a silicon photomultiplier.

(A10) Any scintillation detector denoted by one of (A1) through (A9), may further include a memory and a microprocessor. The memory stores non-transitory computer-readable instructions. The microprocessor is adapted to execute the instructions to estimate lateral coordinates, in a plane of the substrate, of a scintillation-event interaction-position based on a plurality of electrical signal amplitudes and respective plurality of locations of the plurality of photo detectors.

(A11) In any scintillation detector denoted by one of (A1) through (A10), the substrate may include a plurality of optical scatterers.

(A12) In any scintillation detector denoted by (A11), in which the substrate comprising a scintillator material, each of the plurality of optical scatterers may have an extent exceeding a wavelength corresponding to an emission maximum of the scintillator material, or may have a size or extent close to the wavelength corresponding to maximum emission.

(A13) In any scintillation detector denoted by one of (A11) and (A12), the plurality of optical scatterers comprise a through hole, a blind hole, an object on the front surface, an object on the back surface, a volume with modified optical properties generated by laser etching or laser engraving, or combinations thereof.

(B1) A stacked scintillation detector comprising a plurality of scintillation detectors, denoted by (A1), arranged as a stack. The plurality of scintillation detectors comprises a first scintillation detector and a second scintillation detector, the back substrate-surface of the first scintillation detector being adjacent to, opposing, and spatially separated from the front substrate-surface of the second scintillation detector. The stack may comprise two or more, three or more, four or more, five or more, six or more, seven or more, eight or more, nine or more, ten or more, fifteen or more, or twenty or more scintillation detectors.

(B2) In the stacked scintillation detector denoted by (B1), the second scintillation detector may be positioned in relation to the first scintillation detector such that a center region of the second scintillation detector is aligned with a center region of the first scintillation detector relative to an axis perpendicular to the front substrate-surface of the first scintillation detector.

(B3) In the stacked scintillation detector denoted by (B1), the second scintillation detector may be positioned in relation to the first scintillation detector such that a center region of the second scintillation detector is laterally offset from center region of the first scintillation detector relative to an axis perpendicular to the front substrate-surface of the first scintillation detector.

(B4) In any stacked scintillation detector denoted by one of (B1) and (B3), the second scintillation detector may be positioned in relation to the first scintillation detector such that a center region of the second scintillation detector is aligned with an edge surface of the first scintillation detector relative to an axis perpendicular to the front substrate-surface of the first scintillation detector.

(B5) Any stacked scintillation detector denoted by one of (B1) through (B4) may further include a microprocessor configured to receive electrical signals generated by one or more scintillation events from the plurality of photodetectors of at least one of the plurality of scintillation detectors, and configured to estimate lateral coordinates of a gamma-ray interaction position in a plane of the substrate of the at least one of the plurality of scintillation detectors, based on a plurality of electrical signal amplitudes and respective plurality of locations of the plurality of photodetectors.

(B6) In any stacked scintillation detector denoted by (B5), the microprocessor may be further configured to estimate depth coordinates of a scintillation-event interaction-position based on the plurality of electrical signal and respective plurality of locations of the plurality of photodetectors within the stack.

(C1) A PET detector ring comprising a plurality of scintillation detectors denoted by (A1). At least a first sub-plurality of the plurality of scintillation detectors form a first array having (i) a first concave inward-facing surface and including each front surface of the first sub-plurality and (ii) and a first convex outward-facing surface and including each back surface of the first sub-plurality.

(C2) In the PET detector ring denoted by (C1), the plurality of scintillation detectors may comprise a second sub-plurality of scintillation detectors forming a second array having (i) a second concave inward-facing surface, opposite the first convex outward-facing surface, and including each front surface of the second sub-plurality of scintillation detectors and (ii) a second convex outward-facing surface that includes each back surface of the second sub-plurality of scintillation detectors. The PET detector ring may comprise two or more, three or more, four or more, five or more, six or more, seven or more, eight or more, nine or more, ten or more, fifteen or more, twenty or more, fifty or more, or a hundred or more scintillation detectors.

(C3) In the PET detector ring denoted by (C2), the second array may be spatially shifted from the first array such that gamma-ray photons transmitted between photodetectors of adjacent scintillation detectors of the first array are incident on a substrate of a scintillation detector of the second array.

(D1) denotes a method for determining interaction position of a scintillation event, occurring in a substrate resulting from electromagnetic radiation incident on a front surface of the substrate. The method comprises a step of detecting, with a plurality of photodetectors, scintillation light from the gamma-ray interaction event resulting in a respective plurality of electrical signal amplitudes, the plurality of photodetectors being disposed at a respective region around a perimeter of the substrate and having a photosensitive region in optical communication with an edge surface of the substrate located between the front surface and a back surface of the substrate opposite the front surface. The method also includes a step of estimating lateral coordinates, in a plane of the substrate, of the interaction position based on the plurality of electrical signal amplitudes and respective regions.

(D2) In the method denoted by (D1), the substrate may be one of a plurality of stacked scintillator substrates. Each scintillator substrate has (a) a respective edge surface and (b) a respective plurality of photodetectors having a photosensitive region in optical communication with the respective edge surface, the gamma-ray interaction event occurring in one of the plurality of scintillator substrates, the method further comprising determining, from zero and non-zero electrical signal amplitudes from the photodetectors, (i) the one of the plurality of substrates and (ii) an associated depth-of-interaction of the gamma-ray interaction event in a direction perpendicular to the plane of the substrate.

(D3) In any method denoted by one of (D1) and (D2), the step of estimating may include comparing the plurality of electrical signal amplitudes to a mean-detector response function of the plurality of photodetectors at the respective regions around the substrate perimeter.

(D4) In the method denoted by (D3), the step of comparing may include performing at least one of a maximum likelihood estimate, a least-squares estimate, an iterative estimate, a LN norm comparison (where N is 0, 1, 2 . . . ), and an Anger method.

Having now fully described the present invention in some detail by way of illustration and examples for purposes of clarity of understanding, it will be obvious to one of ordinary skill in the art that the same may be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components, or compounds is disclosed herein, it is understood that all individual members of those groups and all subgroups thereof are disclosed separately. Every formulation or combination of components described or exemplified herein may be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

One of ordinary skill in the art will appreciate that starting materials, device elements, analytical methods, mixtures and combinations of components other than those specifically exemplified may be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

The invention claimed is:

1. A positron emission tomography (PET) detector ring comprising:
   a first ring-shaped array of first scintillation detector assemblies, each first scintillation detector assembly including a scintillation detector system that comprises a stack of said scintillation detectors, wherein a chosen scintillation detector of the stack comprises:
   (a) a scintillator element configured as a monolithic optical substrate of a scintillation crystal material that is dimensioned as a thin slab and is materially limited by:
      a front surface configured as an input surface of the detector, a back surface separated from the front surface by a thickness of the monolithic optical substrate, and an edge surface connecting the front and back surfaces; and (b) multiple photodetectors, each of which is disposed to acquire scintillation photons from the body of the element through a respectively-corresponding section of the edge surface, wherein the monolithic optical substrate in configured as a lightguide channeling the scintillation photons generated in the monolithic optical substrate by radiation, which has entered the monolithic optical substrate through the input surface, along the input surface towards and through the edge surface to be acquired by the multiple photodetectors;

wherein each of said scintillation detectors of the stack is configured as said chosen scintillation detector;

wherein each of said scintillation detectors is separated from an immediately-neighboring scintillation detector of the stack by a gap in a direction transverse to respectively-corresponding front surfaces of monolithic optical substrates of the scintillation detectors.

2. A PET detector ring according to claim 1, further comprising:

a second ring-shaped array of second scintillation detector assemblies, each second scintillation detector assembly including said scintillation detector system, wherein at least one of the following conditions is satisfied:

(2a) the first and second ring-shaped arrays are concentric about a center of the PET detector ring; and (2b) the second ring-shaped array is rotatable with respect to the first ring-shaped array about the center.

3. A method for determining a position of a scintillation event with the PET ring according to claim 2, the method comprising:

with at least one scintillation detector of a chosen ring-shaped array, of the first and second ring-shaped arrays:

channeling scintillation photons, generated by said radiation within a monolithic body of the at least one scintillation detector along an input surface of the at least one scintillation detector towards an edge surface of the at least one scintillation detector;

transmitting the scintillation photons through said edge surface towards multiple photodetectors, each of which is disposed at said monolithic body of the at least one scintillation detector to acquire the scintillation photons that have traversed a respectively-corresponding section of said edge surface; and acquiring the scintillation photons that have traversed through said edge surface of the at least one scintillation detector with the multiple photodetectors, with a microprocessor, operably cooperated with said at least one scintillation detector and with a tangible non-transitory storage medium on which are stored microprocessor-readable instructions:

executing the instructions to calculate lateral coordinates, in a plane of the monolithic substrate of said at least one scintillation detector, of said position based on a plurality of amplitudes of electrical signals received from said multiple photodetectors of the at least one scintillation detector and respective plurality of locations of said multiple photodetectors, and estimating, from zero and non-zero amplitudes of electrical signal received from multiple photodetectors of scintillator elements of a stack of said chosen ring-shaped array, at least (i) in which of the scintillator elements of the stack the scintillation event has occurred, and (ii) a depth coordinate of the location of the scintillation event, in a direction perpendicular to a plane of a monolithic substrate of a scintillator element in which the scintillation event has occurred, based on the plurality of amplitudes and respective plurality of locations of multiple photodetectors of the scintillator element in which the scintillation event has occurred.

4. A method according to claim 3, wherein said executing the instructions includes comparing the plurality of amplitudes to a mean-detector response function of the multiple photodetectors of the scintillator elements of the stack of the chosen ring-shaped array.

5. A PET detector ring according to claim 1, wherein an input surface of a monolithic substrate of a scintillation detector of a first scintillation detector assembly is a concave surface facing inwardly towards a center of the PET detector ring, and/or wherein a back surface of the monolithic substrate of the scintillation detector of the first scintillation detector assembly is a convex surface facing outwardly with respect to the center of the PET detector ring.

6. A PET detector ring according to claim 1, further comprising multiple optical couplers respectively corresponding to multiple photodetectors and respectively-corresponding sections of an edge surface of at least one of scintillation detectors of a first scintillation detector assembly of the first ring-shaped array, wherein each of the multiple optical couplers is disposed to receive the scintillation photons only through the respectively-corresponding section of the edge surface and to deliver the received scintillation photons only to a respectively-corresponding detector of the multiple photodetectors.

7. A PET ring according to claim 1, wherein, in a chosen scintillation detector system, a center region of a first scintillation detector of a corresponding stack is spatially aligned with a center region of a second scintillation detector of the corresponding stack along an axis that is perpendicular to a front surface of the first scintillation detector.

8. A PET ring according to claim 1, wherein, in a chosen scintillation detector system, an edge surface of a first scintillation detector of a corresponding stack is laterally offset from an edge surface of a second scintillation detector of the corresponding stack with respect to an axis that is perpendicular to a front surface of the first scintillation detector.

9. A PET ring according to claim 1, wherein a chosen scintillation detector system further comprises:

a material that is optically-opaque and/or optically-reflecting at a wavelength characterizing the scintillation photons and that is disposed between a back surface of a first scintillation detector of a corresponding stack and a front surface of a second scintillation detector of the corresponding stack to reduce transmission of the scintillation photons generated in a monolithic optical substrate of the first scintillation detector to a monolithic optical substrate of the second scintillation detector.

10. A PET ring according to claim 1, further comprising:
a microprocessor, operably cooperated with the multiple photodetectors of at least one scintillation detector of a stack of at least one of constituent scintillation detector systems of the ring, and
a tangible non-transitory storage medium on which are stored data-processor-readable instructions such that, when the instructions are executed by the microprocessor, the instructions cause the microprocessor:
to estimate lateral coordinates, in a plane of a monolithic optical substrate of said at least one scintillation detector, of a location of a scintillation event based on a plurality of amplitudes of electrical signals received from said multiple detectors and respective plurality of locations of said multiple photodetectors,
to estimate energy of the scintillation event, and
to estimate time of occurrence of the scintillation event.

11. A PET ring according to claim 10,
wherein the tangible non-transitory storage medium contains microprocessor-readable instructions which, when the instructions are executed by the microprocessor, cause the microprocessor to estimate depth coordinates of the location of the scintillation event in the monolithic substrate of said at least one scintillation detector based on the plurality of amplitudes of electrical signals received from said multiple detectors and respective plurality of locations of said multiple photodetectors.

12. A PET ring according to claim 1,
wherein a monolithic optical substrate of at least one of the scintillation detector of a stack of at least one of constituent scintillation detector systems of the ring comprises a plurality of optical scatterers spatially distributed throughout a body of said monolithic optical substrate between front and back surfaces of said monolithic optical substrate to cast optical shadows onto at least some sections of an edge surface of said monolithic optical substrate, said sections respectively corresponding to multiple photodetectors of the at least one of the scintillation detector.

13. A PET ring according to claim 1,
wherein at least one layer of a corresponding stack of at least one constituent scintillation detector system of the ring includes multiple scintillation detectors each of which is configured as said chosen scintillation detector, and
wherein an edge surface of a monolithic substrate of a first scintillation detector in a first layer of the stack is laterally offset from an edge surface of a monolithic substrate of a second scintillation detector in a second layer of the corresponding stack with respect to an axis that is perpendicular to the monolithic substrate of the first scintillation detector.

14. A PET ring according to claim 1,
wherein multiple photodetectors of a chosen scintillation detector of at least one of constituent scintillation detector systems of the ring are directly attached to respectively-corresponding sections of an edge surface of a monolithic optical substrate of the chosen scintillation detector.

15. A PET ring according to claim 1, wherein a thickness of the monolithic substrate of the chosen scintillation detector is 2 times to 50 times smaller than each of a length and a width of the front surface and a length and a width of the back surface of said monolithic substrate.

16. A PET ring according to claim 1, wherein the monolithic substrate of the chosen scintillation detector is configured to channel the scintillator photons towards the edge surface of said monolithic substrate by totally internally reflecting said photons at the front and back surfaces of said monolithic substrate.

17. A method for determining a position of a scintillation event with the PET ring according to claim 1, the method comprising:
with at least one scintillation detector of the first ring-shaped array:
channeling scintillation photons, generated by said radiation within a monolithic body of the at least one scintillation detector along an input surface of the at least one scintillation detector towards an edge surface of the at least one scintillation detector;
transmitting the scintillation photons through said edge surface towards multiple photodetectors, each of which is disposed at said monolithic body of the at least one scintillation detector to acquire the scintillation photons that have traversed a respectively-corresponding section of said edge surface; and
acquiring the scintillation photons that have traversed through said edge surface of the at least one scintillation detector with the multiple photodetectors,
with a microprocessor, operably cooperated with said at least one scintillation detector and with a tangible non-transitory storage medium on which are stored microprocessor-readable instructions:
executing the instructions to calculate lateral coordinates, in a plane of the monolithic substrate of said at least one scintillation detector, of said position based on a plurality of amplitudes of electrical signals received from said multiple photodetectors of the at least one scintillation detector and respective plurality of locations of said multiple photodetectors, and
estimating, from zero and non-zero amplitudes of electrical signal received from multiple photodetectors of scintillator elements of a stack of the first ring-shaped array, at least (i) in which of the scintillator elements of the stack the scintillation event has occurred, and (ii) a depth coordinate of the location of the scintillation event, in a direction perpendicular to a plane of a monolithic substrate of a scintillator element in which the scintillation event has occurred, based on the plurality of amplitudes and respective plurality of locations of multiple photodetectors of the scintillator element in which the scintillation event has occurred.

* * * * *